US009278952B2

(12) United States Patent
Conza et al.

(10) Patent No.: US 9,278,952 B2
(45) Date of Patent: Mar. 8, 2016

(54) BENZOIMIDAZOL-2-YL PYRIMIDINE MODULATORS OF THE HISTAMINE $H_4$ RECEPTOR

(71) Applicant: Janssen Pharmaceutica NV, Beerse (BE)

(72) Inventors: Matteo Conza, Thayngen (CH); Magali B. Hickey, Westwood, MA (US); Stefan Horns, Schaffhausen (CH); Susanne Lochner, Singen (DE)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

(21) Appl. No.: 14/465,677

(22) Filed: Aug. 21, 2014

(65) Prior Publication Data

US 2014/0364607 A1 Dec. 11, 2014

Related U.S. Application Data

(63) Continuation of application No. 14/199,634, filed on Mar. 6, 2014, now Pat. No. 8,859,575.

(60) Provisional application No. 61/773,706, filed on Mar. 6, 2013, provisional application No. 61/776,260, filed on Mar. 11, 2013, provisional application No. 61/784,909, filed on Mar. 14, 2013.

(51) Int. Cl.
*C07D 401/14* (2006.01)

(52) U.S. Cl.
CPC .................................. *C07D 401/14* (2013.01)

(58) Field of Classification Search
USPC .......................................... 544/331; 514/275
See application file for complete search history.

(56) References Cited

U.S. PATENT DOCUMENTS

| 3,005,852 | A | 10/1961 | Freyermuth |
|---|---|---|---|
| 3,609,152 | A | 9/1971 | Hess |
| 3,931,195 | A | 1/1976 | Dykstra |
| 4,190,601 | A | 2/1980 | Decker |
| 4,191,828 | A | 3/1980 | Horgan |
| 4,337,341 | A | 6/1982 | Zimmerman |
| 5,614,524 | A | 3/1997 | Matassa et al. |
| 5,621,097 | A | 4/1997 | Brown |
| 5,880,140 | A | 3/1999 | Anthony |
| 5,883,105 | A | 3/1999 | Anthony |
| 5,939,439 | A | 8/1999 | Anthony et al. |
| 5,945,422 | A | 8/1999 | Doherty |
| 6,051,574 | A | 4/2000 | Anthony |
| 6,077,853 | A | 6/2000 | Graham et al. |
| 6,210,394 | B1 | 4/2001 | Demopulos et al. |
| 6,242,460 | B1 | 6/2001 | Ettema |
| 6,372,743 | B1 | 4/2002 | Darrow |
| 6,624,180 | B2 | 9/2003 | South et al. |
| 6,693,194 | B2 | 2/2004 | Jau et al. |
| 6,828,338 | B2 | 12/2004 | South et al. |
| 6,835,726 | B2 | 12/2004 | Cushing |
| 6,858,600 | B2 | 2/2005 | Hamilton et al. |
| 6,916,938 | B2 | 7/2005 | Oguma |
| 6,989,383 | B1 | 1/2006 | Rosen et al. |
| 7,148,236 | B2 | 12/2006 | Astles et al. |
| 7,250,427 | B2 | 7/2007 | Breitenbucher et al. |
| 7,312,246 | B2 | 12/2007 | Hamilton et al. |
| 7,314,937 | B2 | 1/2008 | Beavers et al. |
| 7,405,221 | B2 | 7/2008 | Kopka et al. |
| 7,507,737 | B2 | 3/2009 | Edwards et al. |
| 7,576,095 | B2 | 8/2009 | Chavez |
| 7,923,451 | B2 | 4/2011 | Edwards et al. |
| 7,928,131 | B2 | 4/2011 | Buzard et al. |
| 8,084,466 | B2 | 12/2011 | Kindrachuk et al. |
| 8,309,720 | B2 | 11/2012 | Cesco-Cancian |
| 8,343,989 | B2 | 1/2013 | Edwards et al. |
| 8,598,189 | B2 | 12/2013 | Edwards et al. |
| 8,841,287 | B2 | 9/2014 | Cai et al. |
| 8,859,575 | B2 | 10/2014 | Conza et al. |
| 2002/0077332 | A1 | 6/2002 | Aronhime |
| 2003/0187026 | A1 | 10/2003 | Li et al. |
| 2003/0207893 | A1 | 11/2003 | Carruthers et al. |
| 2004/0048878 | A1 | 3/2004 | Cui et al. |
| 2004/0058934 | A1 | 3/2004 | Carruthers et al. |
| 2004/0105856 | A1 | 6/2004 | Thurmond et al. |
| 2004/0127395 | A1 | 7/2004 | Desai |
| 2004/0132715 | A1 | 7/2004 | Dunford et al. |
| 2004/0224964 | A1 | 11/2004 | O'Yang |
| 2004/0261190 | A1 | 12/2004 | Eggenweiler |
| 2005/0070527 | A1 | 3/2005 | Edwards et al. |
| 2005/0070550 | A1 | 3/2005 | Arienti et al. |

(Continued)

FOREIGN PATENT DOCUMENTS

| JP | 61030576 A | 2/1986 |
|---|---|---|
| WO | WO97/36890 | 10/1997 |

(Continued)

OTHER PUBLICATIONS

Amin et al. "Inflammation and Structural Changes in the Airways of Patients with Atopic and NonAtopic Asthma" Am J Resp. Crit Care Med 2000 vol. 162(6) pp. 2295-2301.
Altenbach, R. et al. Structure-Activity Studies on a Series of a 2-Aminopyrimidine-Containing Histamine H4 Receptor Ligands. Jour. Med. Chem. 2008. vol. 51(20), 6571-6580.
Bagshawe et al. "Antibody-Directed Enzyme Prodrug Therapy: A Review" Drug Dev Res 1995 vol. 34 pp. 220-230.
Bell et al "Involvement of Histamine $H_4$ and $H_1$ Receptors in Scratching Induced by Histamine Receptor Agonists in BalbC Mice" Br J Pharmaol 2004 vol. 142(2) pp. 374-380.
Benoist et al "Mast Cells in Autoimmune Disease" Nature 2002 vol. 420(6917) pp. 875-878.
Berge et al. "Pharmaceutical Salts" Journal of Pharmaceutical Sciences 1977 vol. 66(1) pp. 1-19.
Bertolini et al. "A New Rational Hypothesis for the Pharmacophore of the Active Metabolite of Leflunomide, A Potent Immunosuppressive Drug" J Med Chem 1997 vol. 40 pp. 2011-2016.
Bodor et al. "Novel Approaches to the Design of Safer Drugs: Soft Drugs and Site-Specific Chemical Delivery Systems" Advances in Drug Research 1984 vol. 13 pp. 224-331.

(Continued)

*Primary Examiner* — Kristin Vajda

(57) ABSTRACT

Benzoimidazol-2-yl pyrimidines, purification methods for the same, and pharmaceutical compositions and methods for the treatment of disease states, disorders, and conditions mediated by $H_4$ receptor activity, including allergy, asthma, autoimmune diseases, and pruritus.

14 Claims, 9 Drawing Sheets

(56) References Cited

U.S. PATENT DOCUMENTS

| | | |
|---|---|---|
| 2005/0181023 A1 | 8/2005 | Young et al. |
| 2005/0261309 A1 | 11/2005 | Buzard et al. |
| 2006/0089496 A1 | 4/2006 | Lam et al. |
| 2006/0281712 A1 | 12/2006 | Yen et al. |
| 2007/0043043 A1 | 2/2007 | Chen et al. |
| 2007/0099938 A1 | 5/2007 | Ohmoto et al. |
| 2007/0185163 A1 | 8/2007 | Hunt et al. |
| 2007/0232616 A1 | 10/2007 | Edwards et al. |
| 2007/0238771 A1 | 10/2007 | Edwards et al. |
| 2007/0244126 A1 | 10/2007 | Edwards et al. |
| 2007/0265250 A1 | 11/2007 | Buzard et al. |
| 2008/0119494 A1 | 5/2008 | Young et al. |
| 2008/0132513 A1 | 6/2008 | Che |
| 2008/0267887 A1 | 10/2008 | Yuan et al. |
| 2009/0137608 A1 | 5/2009 | Edwards et al. |
| 2009/0143302 A1 | 6/2009 | Yen et al. |
| 2009/0182142 A1 | 7/2009 | Furukubo et al. |
| 2010/0029942 A1 | 2/2010 | Cesco-Cancian et al. |
| 2011/0076324 A1 | 3/2011 | Thurmond |
| 2011/0184016 A1 | 7/2011 | Lerner |
| 2012/0178932 A1 | 7/2012 | Cesco-Cancian et al. |
| 2012/0184740 A1 | 7/2012 | Cesco-Cancian et al. |
| 2013/0053561 A1 | 2/2013 | Cesco-Cancian |
| 2013/0202685 A1 | 8/2013 | Thurmond |
| 2013/0225816 A1 | 8/2013 | Cesco-Cancian |
| 2014/0038995 A1 | 2/2014 | Edwards |
| 2014/0066624 A1 | 3/2014 | Cesco-Cancian |
| 2014/0073795 A1 | 3/2014 | Cesco-Cancian |
| 2014/0121374 A1 | 5/2014 | Cesco-Cancian |

FOREIGN PATENT DOCUMENTS

| | | |
|---|---|---|
| WO | WO97/36898 | 10/1997 |
| WO | WO 98 31369 A1 | 7/1998 |
| WO | WO98/44797 | 10/1998 |
| WO | WO 99 18079 A1 | 4/1999 |
| WO | WO99/41253 | 9/1999 |
| WO | WO 99 65897 A1 | 12/1999 |
| WO | WO 01 00610 A1 | 1/2001 |
| WO | WO01/14376 | 3/2001 |
| WO | WO 01 47883 A1 | 5/2001 |
| WO | WO01/58871 | 8/2001 |
| WO | WO 02 00847 A1 | 1/2002 |
| WO | WO 02 20495 A2 | 3/2002 |
| WO | WO02/78701 | 3/2002 |
| WO | WO02/064096 | 8/2002 |
| WO | 02/072548 A2 | 9/2002 |
| WO | WO 02 076438 A2 | 10/2002 |
| WO | WO 03 000254 A1 | 3/2003 |
| WO | WO 03 051366 A2 | 6/2003 |
| WO | WO 2004 012736 A1 | 2/2004 |
| WO | WO 2004 030625 A2 | 4/2004 |
| WO | WO2004/110350 | 12/2004 |
| WO | WO 2004 110350 A2 | 12/2004 |
| WO | WO 2005 032490 A2 | 4/2005 |
| WO | WO2005/040135 | 4/2005 |
| WO | WO 2005 039485 A2 | 5/2005 |
| WO | WO 2005 044807 A2 | 5/2005 |
| WO | WO2005/092066 | 10/2005 |
| WO | WO2005/115993 | 11/2005 |
| WO | WO2006/025567 | 3/2006 |
| WO | WO2006/063466 | 6/2006 |
| WO | WO2006/102645 | 9/2006 |
| WO | WO2006/138304 | 12/2006 |
| WO | WO2007/003604 | 1/2007 |
| WO | WO 2007 003604 A2 | 1/2007 |
| WO | WO 2007/031529 | 3/2007 |
| WO | WO2007/044085 | 4/2007 |
| WO | WO2007/059610 | 5/2007 |
| WO | WO 2007 070173 A2 | 6/2007 |
| WO | WO2007/095753 | 8/2007 |
| WO | WO 2007 117399 A2 | 10/2007 |
| WO | WO2007/117400 | 10/2007 |
| WO | WO 2007/120690 | 10/2007 |
| WO | WO 2007 120690 A2 | 10/2007 |
| WO | WO2007/124589 | 11/2007 |
| WO | WO2007/134434 | 11/2007 |
| WO | WO 2009 068512 A1 | 6/2009 |
| WO | WO 2009/152287 | 12/2009 |
| WO | WO2010/002774 | 1/2010 |
| WO | WO2010/002777 | 1/2010 |
| WO | WO2012/060590 | 5/2012 |
| WO | WO2012/069442 | 5/2012 |

OTHER PUBLICATIONS

Buckland et al "Histamine Induces Cytoskeletal Changes in Human Eosinophils via the $H_4$ Receptor" Br J Pharmacol 2003 vol. 140(6) pp. 1117-1127.
Bundgaard "Design of Prodrugs" 1985 Ed. Hans Bundgaard p. 1.
Cheng et al. "Relationship Between the Inhibition Constant ($K_1$) and the Concentration of Inhibitor Which Causes 50 Percent Inhibition ($I_{50}$) of an Enzymatic Reaction" Biochem Pharmacol 1973 vol. 22 pp. 3099-3108.
Coge et al "Structure and Expression of the Human Histamine $H_4$-Receptor Gene" Biochem Biophys Res Commun 2001 vol. 284(2) pp. 301-309.
Cohen J. "The Immunopathogenesis of Sepsis" Nature 2002 vol. 420(6917) pp. 885-891.
Coussens et al "Inflammation and Cancer" Nature 2002 vol. 420(6917) pp. 860-867.
Crimi et al "Increased Numbers of Mast Cells in Bronchial Mucosa After the Late Phase Asthmatic Response to Allergen" Am Rev Respir Dis 1991 vol. 144(6) pp. 1282-1286.
de Esch et al. "The Histamine $H_4$ Receptor as a New Therapeutic Target for Inflammation" Trends Pharmacol Sci 2005 vol. 26(9) pp. 462-469.
Dunford, P.J. et al. The histamine H4 receptor mediates allergic airway inflammation by regulating the activation of CD4+T cells. Journal of Immunology, 2006. vol. 176(11), 7062-7070.
Dunford, P.J. et al. Histamine H4 receptor antagonists are superior to traditional antihistamines in the attenuation of experimental pruritus. J. Allergy Clin. Immunol. 2007, vol. 119(1), 176-183.
Fleisher et al. "Improved Oral Delivery: Solubility Limitations Overcome by the Use of Prodrugs" Advanced Drug Delivery Review 1996 vol. 19 pp. 115-130.
Fokkens et al "Dynamics of Mast Cells in the Nasal Mucosa of Patients with Allergic Rhinitis and Non-Allergic Controls: A Biopsy Study" Clin Exp Allergy 1992 vol. 22(7) pp. 701-710.
Fung-Leung et al. "Histamine $H_4$ Receptor Antagonists: The New Antihistamines?" Curr Opin Invest Drugs 2004 vol. 5(11) pp. 1174-1183.
Gantner et al. "Histamines $H_4$ and $H_2$ Receptors Control Histamine-Induced Interleukin-16 Release from Human CD8+T Cells" J Pharmacol Exp 2002 vol. 303(1) pp. 300-307.
Gauvreau et al "Increased Numbers of Both Airway Basophils and Mast Cells in Sputum after Allergen Inhalation Challenge of Atopic Asthmatics" Am J Resp Crit Care Med 2002 vol. 161(5) pp. 1473-1478.
Gutzmer et al "Histamine $H^4$ Receptor Stimulation Suppresses IL-12p70 Production and Mediates Chemotaxis in Human Monocyte-Derived Dendritic Cells" J Immunol 2005 vol. 174(9) pp. 5224-5232.
Hofstra et al "Histamine $H^4$ Receptor Mediates Chemotaxis and Calcium Mobilization of Mast Cells" J Pharmacol Exp Ther 2003 vol. 305(3) pp. 1212-1221.
Horr et al. STAT1 phosphorylation and cleavage is regulated by the histamine (H4) receptor in human atopic and non-atopic lymphocytes. International Immunopharmacology 2006, vol. 6 (10), 1577-1585.
Ikawa et al "Histamine $H^4$ Receptor Expression in Human Synovial Cells Obtained from Patients Suffering from Rheumatoid Arthristis" Biol Pharm Bull 2005 vol. 28(10) pp. 2016-2018.
Jablonowski, J. et al., The first potent and selective non-imidazole human histamine H4 receptor antagonists. Journal of Medicinal Chemistry, 2003. vol. 46(19), 3957-3960.
Jiang et al. Cloning and pharmacological characterization of the dog histamine H-4 receptor. European Journal of Pharmacology, 2008. vol. 592(1-3), 26-32.

(56) References Cited

OTHER PUBLICATIONS

Jokuti et al. Histamine H4 receptor expression is elevated in human nasal polyp tissue, Cell Biology International. 2007 vol. 31(11) 1367-1370.
Kassel et al. "Local Increase in the Number of Mast Cells and Expression of Nerve Growth Factor in the Bronchus of Asthmatic Patients after Repeated Inhalation of Allergen Low-Dose" Clin Exp Allergy 2001 vol. 31(9) pp. 1432-1440.
Kirby et al "Bronchoalveolar Cell Profiles of Asthmatic and NonAsthmatic Subjects" Am. Rev. Respir. Dis. 1987, vol. 136(2) pp. 379-383.
Kiss, R. et al. Histamine H4 receptor ligands and their potential therapeutic applications. Expert Opin. Ther. Patents, 2009, vol. 19(2), 119-135.
Krug et al "Interleukin 16 and T-cell Chemoattractant Activity in Bronchoalveolar Lavage 24 Hours After Allergen Challenge in Asthma" Am J Resp Crit Care Med 2000 vol. 162(1) pp. 105-111.
Lee-Dutra, A. et al., Identification of 2-arylbenzimidazoles as potent human histamine H-4 receptor ligands, Bioorganic & Medicinal Chemistry Letters 2006. vol. 16(23), 6043-6048.
Leite-de-Moraes, Cutting edge: histamine receptor H4 activation positively regulates in vivo IL-4 and IFN-gamma production by invariant NKT cells. Journal of Immunology, 2009. 182(3):1233-1236.
Libby P. "Inflammation in Atherosclerosis" Nature 2002 vol. 420 pp. 868-874.
Lim, H. et al., Evaluation of histamine H-1-, H-2-, and H-3-receptor ligands at the human histamine H-4 receptor: Identification of 4-methylhistamine as the first potent and selective H-4 receptor agonist. Journal of Pharmacology & Experimental Therapeutics, 2005, vol. 314(3), 1310-1321.
Ling et al. "Histamine $H^4$ Receptor Mediates Eosiniphil Chemolaxis with Cell Shape Change and Adhesion Molecule Upregulation" Br J. Pharmacol 2004 vol. 142(1) pp. 161-171.
Lippert et al "Human Skin Cells Express H2 and H4, but not H3 Receptors" J Invest Dermatol 2004 vol. 123(1) pp. 116-123.
Liu et al "Cloning of Pharmacological Characterization of a Fourth Histamine Receptor ($H^4$) Expressed in Bone Marro" Mol Pharmacol 2001 vol. 59(3) pp. 420-426.
Mashikian et al "Identification of IL-16 as the Lymphocyte Chemotactic Activity in the Bronchoalveolar Lavage Fluid of Histamine-Challenged Asthmatic Patients" J Allergy Clin Immunol 1998 vol. 101(6 Part 1) pp. 786-792.
Morse et al "Cloning and Characterization of Novel Human Histamine Receptor" J Pharmacol Exp. Ther 2001 vol. 296(3) pp. 1058-1066.
Nathan C. "Points of Control in Inflammation" Nature 2002 vol. 420(6917) pp. 846-852.
O'Reilly et al "Identification of $H^4$ Receptor in Human Eosinophilis—Role in Eosinophil Chemotaxis" J Recept Signal Transduction 2002 vol. 22(1-4) pp. 431-448.
Parsons et al. "Histamine and Its Receptors" British Jurnal of Pharmacology 2006 vol. 147 pp. S127-S135.
Robinson et al "Discovery of the Hemifumarate and (α-L-Alanyloxy)methyl Ester as Prodrugs of an Antirheumatic Oxindole: Prodrugs for the Enolic OH Group" J Med Chem 1996 vol. 39 pp. 10-18.
Robinson Malcom "Medical Therapy of Inflammatory Bowel Disease for the $21^{st}$ Century" Eur J. Surg 1998 Suppl 582 pp. 90-98.
Shan et al. "Prodrug Strategies Based on Intramolecular Cyclization Reactions" Journal of Pharmaceutical Sciences 1997 vol. 86(7) pp. 765-767.
Silverman Richard B. "Prodrugs and Drug Delivery Systems" The Organic Chemistry of Drug Design and Drug Action 1997 Chapter 8 pp. 353-399.
Singh et al. "Immune Therapy in Inflammation Bowel Disease and Models Colitis" British Journal of Surgery 2001 vol. 88 pp. 1558-1569.
Slater et al "Increase in epithelial Mast Cell Numbers in the Nasal Mucosa of Patients with Perennial Allergic Rhinitis" J Laryngol Otol 1996 vol. 110 pp. 929-933.
Smits, R.A. et al. Major advances in the development of histamine H4 receptor ligands. Drug Discovery Today, 2009, vol. 14(15-16):745-753.
Steinberg D. "Atherogenesis in Perspective: Hypercholesterolemia and Inflammation as Partners in Crime" Nature Med 2002 vol. 8(11) pp. 1211-1217.
Takeshita et al "Critical Role of Histamine $H_4$ Receptor in Leukotriene $B_4$ Production and Mast-Cell Dependent Neutrophil Recruitment Induced by Zymosan in Vivo" J Pharmacol Exp Ther 2003 vol. 307(3) pp. 1072-1078.
Terzioglu et al. "Synthesis and Structure-Activity Relationship of Indole and Benzimidazole Piperazines as Histamine $H_4$ Receptor Antagonists" Bioorg & Med Chemistry Letters 2004 vol. 14 pp. 5251-5256.
Testa et al "Predicting Drug Metabolism: Concepts and Challenges" Pure Appl Chem 2004 vol. 76(5) pp. 907-914.
Thurmond et al "A Potent and Selective Histamine H4 Receptor Antagonist with Anti-Inflammatory Properties" J Pharmacol Exp Ther 2004 vol. 309(1) pp. 404-413.
Thurmond R. L. et al , The role of histamine H1 and H4 receptors in allergic inflammation: the search for new antihistamines. Nat. Rev. Drug Disc. 2008 vol. 7(1), 45-53.
Tracey K. J. "The Inflammatory Reflex" Nature 2002 vol. 420(6917) pp. 853-859.
Varga et al "Inhibitory Effects of Histamine $H^4$ Receptor Antagonists on Experimental Colitis in the Rat" Eur J Pharmacol 2005 vol. 522(1-3) pp. 130-138.
Venable, J.D. et al. Preparation and biological evaluation of indole, benzimidazole, and thienopyrrole piperazine carboxamides: Potent human histamine $H_4$ antagonists. Journal of Medicinal Chemistry, 2005. vol. 48(26), 8289-8298.
Voehringer et al "Type 2 Immunity Reflects Orchestrated Recruitment of Cells Committed to IL-4 Production" Immunity 2004 vol. 20(3) pp. 267-277.
Weiner et al "Inflammation and Therapeutic Vaccination in CNS Diseases" Nature 2002 vol. 420(6917) pp. 879-884.
Zhang, M. et al. The histamine $H_4$ receptor in autoimmune disease. Expert Opinion on Investigational Drugs, 2006. vol. 15(11), 1443-1452.
Zhang, M. et al. The Histamine H4 Receptor: A Novel Mediator of Inflammatory and Immune Disorders. Pharmacol. Ther. 2007. vol. 113, 594-606.
Zhichkin et al. "A General Procedure for the Synthesis of 2-Substituted Pyrimidine-5-Carboxylic Esters" Synthesis 2002 vol. 6 pp. 720-722.
European Journal of Obstetrics & Gynecology and Reproductive Biology 2003, vol. 106, pp. 50-54.
diZerega, G.S. et al., (1992) Prevention of Postoperative Adhesions in "The Peritoneum" Eds. Springer-Verlag, New York, pp. 307-369.
Rodgers, K.E., et al., (1990) "Nonsteroidal Anti-Inflammatory Drugs (NSAIDs) in the treatment of Postsurgical Adhesion" Treatment of Post-Surgical Adhesions, pp. 119-129.
Abarghaz, M. et al., "Regioselective Alkylation of the Exocyclic Nitrogen of Heterocyclic Amides via the Mitsunobu Reaction", Tetrahedron Letters, 1995, vol. 36, pp. 6463-6466.
Lim, H.D., et al, "Molecular determinants of ligand binding to H4R species variants" Mol. Pharmacol. 2010, 77 (5), 734-743.
Venable, J.D., et al. "Development and chemistry of histamine H4 receptor ligands as potential modulators of inflammatory and allergic diseases" Anti-Inflamm Anti-Allergy Agents in Med Chem. 2006, 5 (4), 307-322.
Schneider E.H., et al. "Structural requirements for inverse agonism and neutral antagonism of indole-, benzimidazole-, and thienopyrrole-derived histamine H4 receptor ligands" J. Pharmacol Exp Ther 2010, 334 (2) 513-521.
Savall, B.M., et al. "Agonist/antagonist modulation in a series of 2-aryl benzimidazole H4 receptor ligands" Bioorg Med Chem Lett, 2010, 20(11), 3367-3371.
Dunford, P.J., et al. "Histamine H4 receptor antagonists", Prog Respir Res, 2010, 11, 86.

(56) References Cited

OTHER PUBLICATIONS

Short et al., "Sympathetic Nervous System Blocking Agents. Derivatives of Guanidine and Related Compounds." J. Med. Chem., 1963, 6, 275-283.
Kumar et al., "Design, Synthesis and Biological Evaluation of 1,3-diaminopropanes: A new Class of Polyamine Analogs as Leishmanicidal Agents", Bioorg Med Chem Lett, 1997, 7(6), 675-680.
English, et al., Journal of the American Chemical Society, 1946, 68, 1039-1049.
Brown, et al.,Journal of the Chemical Society [Section C], Organic, 1967, (19), 1928-1933.
Mitsutoshi Tominaga, "Histamine $H_4$ receptor antagonists ineffective against itch and skin inflammation in atopic dermatitis mouse model", $7^{th}$ World Congress on Itch (WCI) Sep. 21-23, 2013, Boston, USA, Oral Presentation.
Mitsutoshi Tominaga. International Investigative Dermatology, "Histamine H4 receptor antagonists exhibit insufficient anti-pruritic and anti-inflammatory effects on mite extract ointment-induced mouse model of atopic dermatitis", May 8-11, 2013, Edinburgh, Scotland, Oral Presentation, Abstract provided.
Savall, B.M. et al., "6-Alkyl-2-aminopyrimidines as Potent Histamine H4 Receptor Antagonists", Gordon Research Conference Medicinal Chemistry, Aug. 5-10, 2012.
Venable, J. "Discovery, SAR, and functional consequences of various 2-heteroarylbenzimidazoles at the human histamine H4 receptor of 2-heteroarylbenzimidazoles", 67th Southwest Regional Meeting of the American Chemical Society, Austin, TX, United States, Nov. 9-12, 2011, SWRM-183.
Venable, J. "Synthesis and SAR of 2-Pyridinylbenzimidazoles as Human Histamine $H_4$ Antagonists", CHI Drug Discovery Chemistry, Apr. 27-28, 2010 • San Diego, CA.
Venable , J, "Novel Modulators of the Human Histamine $H_4$ Receptor", California Institute of Technology, Pasadena, California Apr. 6, 2011.
Venable, J, "Discovery and Development of Human Histamine $H_4$ Antagonists", Medicinal Chemistry Symposium, University of California, San Diego, Jul. 12, 2013.
Venable J., "Synthesis and SAR of 2-Pyridinylbenzimidazoles as Human Histamine $H_4$ Antagonists", 239th ACS National Meeting, San Francisco, CA, United States, Mar. 21-25, 2010, MEDI-14.
Edwards, J. P.,"Ten(+) Years of Histamine H4 Antagonists at Janssen", The Scott E. Denmark Symposium, University of Illinios, Urbana-Champaign, IL. Aug. 3, 2013.
Edwards, J. P., "Ten(+) Years of Histamine H4 Antagonists at Janssen", GTC Novel Immunotherapeutics Summit, Jan. 31, 2013.
Edwards, J. P. "What's Out There?" University of California, San Diego, Jan. 13, 2014.
Lee, A. et al., "Development of Benzimidazole Ligands for the H4 Receptor", 229th ACS National Meeting, San Diego, CA, United States, Mar. 13-17, 2005, MEDI-052.
Thurmond, R. L.; "Histamine H4 Receptor Antagonists as Future Anti-Inflammatory Drugs", European Academy of Allergology and Clinical Immunology, London, UK Jun. 8, 2010.
Cowden, J. M.; et al., The Histamine H4 Receptor Mediates Inflammation in Th2-dependent Dermal Inflammation European Histamine Research Society Meeting, Fulda, Germany May 14, 2009.
Katsunori Yamaura, Joint Symposium of the Japanese Society of Toxicology and the Japanese Society of Immunotoxicology, "Long-term topical steroids treatment and skin toxicity characterized by pruritus" Jul. 2014, Oral Presentation.
Seiji Onuma, et al., General session of The Japanese Society of Toxicology, "Usefulness of the histamine H4 receptor antagonist on exacerbation of pruritus induced by long-term topical steroids treatment", Jul. 2014, Oral Presentation.
Wolfgang Bäumer et al., International Symposium on Atopic Dermatitis, Munich, Germany "Lack of preventing effect of systemically and topically administered histamine $H_4$ receptor antagonists in a canine model of atopic dermatitis" Jul. 22, 2010.
Thurmond, R. L.; "The Role of the Histamine $H_4$ Receptor in Allergy and Inflammation", European Histamine Research Society Meeting Sochi, Russia May 13, 2011.
Thurmond, R. L.; "Clinical Development of Histamine $H_4$ Receptor Antagonists", Lecture at University of Hanover, Germany May 12, 2014.
Thurmond, R. L.; "The Role of the Histamine $H_4$ Receptor in Allergy and Inflammation", Lecture at University of Hanover, Germany May 17, 2011.
Thurmond, R. L.; "The Histamine $H_4$ Receptor and Immune Function", Japanese Society of Immunotoxicity, Chiba, Japan Sep. 8, 2011.
Thurmond, R. L.; "Frontiers in Histamine Research", American Academy of Allergy, Asthma and Immunology, San Francisco, CA, Mar. 18-22, 2011.
Thurmond, R. L.; "The Role of the Histamine H4 Receptor in Allergy and Inflammation", Allergy Drug Discovery and Development Conference, San Diego, CA Jan. 30, 2012.
Cowden, J.M. et al., "Antagonism of the Histamine $H_4$ Receptor Reduces LPS-induced TNF Production In Vivo", European Histamine Research Society Meeting, Belfast, UK May 4, 2012.
Thurmond, R. L.;"Novel Antihistamines that Target the Histamine $H_4$ Receptor", Experimental Biology Meeting, San Diego, CA, Apr. 22, 2012.
Dunford, P.J., et al., "The Histamine H4 Receptor Drives Inflammation in Preclinical Models of Arthritis", American College of Rheumatology, 2013.
Thurmond, R.L., "The Development of Histamine $H_4$ Receptor Antagonists", Japanese Society of Toxicology Chiba Japan Jun. 18, 2013.
Thurmond, R. L. et al., "The Histamine $H_4$ Receptor Mediates Inflammation and Pruritus in Th2-dependent Dermal Inflammation", International Congress of Immunology, Kobe, Japan Aug. 22-27, 2010.
Cowden, J.M. et al., "The Histamine $H_4$ Receptor Mediates Inflammation in Models of Arthritis via Inhibition of Th17", International Congress of Immunology, Milan, Italy Aug. 27, 2013.
Mitsutoshi Tominaga. "Histamine $H_4$ receptor antagonists exhibit insufficient anti-pruritic and anti-inflammatory effects on mite extract ointment-induced mouse model of atopic dermatitis", International Investigative Dermatology, May 8-11, 2013, Edinburgh, Scotland.
Onuma, S."Usefulness of the histamine $H_4$ receptor antagonist on exacerbation of pruritus induced by long-term topical steroids treatment", Japanese Society of Toxicology Jul. 2-4, 2014.
W. Bäumer et al., "Histamine $H_1$ and $H_4$ Receptor Antagonists Do Not Prevent Acute Skin Lesions in a Canine Model of Atopic Dermatitis", European Histamine Research Society Meeting Sochi, Russia May 12, 2011, Oral Presentation.
Thurmond, R. L.; "Histamine H4 Receptor Antagonists New Antihistamines for Itch", 21st Annual Meeting of the International Symposium of Itch,Osaka, Japan Oct. 29, 2011.
Thurmond, R. L.; "The Role of the Histamine H4 Receptor in Allergy and Inflammation", Lecture at University of Vermont, Burlington, VT Nov. 5, 2010.
Thurmond, R. L.; "The Histamine H4 Receptor and Immune Function", Lecture at Tohoku University Sendai, Japan Sep. 7, 2011.
Thurmond, R. L.; "The Role of the Histamine H4 Receptor in Allergy and Inflammation", Lecture at Queen's University Belfast, UK May 1, 2012.
Ulrich, J and Stelzer, T. (2001) Kirk-Othmer Encyclopedia of Chemical Technology, "Crystallization", 1-63.
Dibb, Karin, et al., "The histamine H4 receptor is a potent inhibitor of adhesion-dependent degranulation in human neutrophils", J. Leukocyte Biol, 2014, vol. 96, p. 1-8.
Savall, B.M., et al., Selective phenol alkylation for an improved synthesis of 2-arylbenzimidazole H4 receptor ligands, Tetrahedron Letters 50 (2009) 2490-2492.
Thurmond, R. L.; "Histamine H4 Receptor Antagonists as Future Anti-Inflammatory Drugs", 27th Noordwijkerhout-Camerino-Cyprus Symposium, Noordwijkerhout, Netherlands, May 5, 2009.

(56) References Cited

OTHER PUBLICATIONS

Thurmond, R. L., et al, "Clinical and Preclinical Characterization of the Histamine H4 Receptor Antagonists JNJ-39758979", J Pharmacol Exp Ther 349:176-184, May 2014.
Lochner, S. and Broggini, D. "Impurity Management Progressing from Early to Late Phase Development", 30th SCI Process Development Symposium, Cambridge, England, Dec. 7, 2012.
Baumer, W., et. al., "Lack of preventing effect of systemically and topically administered histamine H1 or H4 receptor antagonists in a dog model of acute atopic dermatitis", Experimental Dermatology, 2011, pp. 1-5.
Desai, P. and Thurmond, R. L., "Histamine H4 receptor activation enhances LPS-induced IL-6 production in mast cells via ERK and PI3K activation", Eur. J. Immunol. 2011. 41: 1764-1773.
Cowden, J. M., et al., "The Histamine H4 Receptor Mediates Inflammation and Pruritus in Th2-Dependent Dermal Inflammation", Journal of Investigative Dermatology (2010) 130, 1023-1033.
Cowden, J. M., et al., Antagonism of the histamine H4 receptor reduces LPS-induced TNF production in vivo, Inflamm. Res. (2013) 62:599-607.
Savall, B. M., et al., "Discovery and SAR of 6-Alkyl-2,4-diaminopyrimidines as Histamine H4 Receptor Antagonists", J. Med. Chem. 2014, 57(6), 2429-2439.
A Kamo et al., "Histamine H4 Receptor Antagonists Ineffective against Itch and Skin Inflammation in Atopic Dermatitis Mouse Model", Journal of Investigative Dermatology (2014) 134, 546-548.
Cowden, J. M., et al., "The histamine H4 receptor mediates inflammation and Th17 responses in preclinical models of arthritis", Ann Rheum Dis 2014;73:600-608.
Istyastono, E. P., et al, "Molecular Determinants of Selective Agonist and Antagonist Binding to the Histamine H4 Receptor", Current Topics in Medicinal Chemistry, 2011, 11, 661-679.
Savall, B. M. et al., "Tricyclic aminopyrimidine histamine H4 receptor antagonists", Bioorganic & Medicinal Chemistry Letters 21 (2011) 6577-6581.
Saskia Nijmeijer,, et al, "Molecular pharmacology of histamine H4 receptors", Frontiers in Bioscience, 17, 2089-2106, Jun. 1, 2012.
Kiss, R., et al., "Histamine H4 receptor ligands and their potential therapeutic applications: an update", Expert. Opin. Ther. Patents (2012) 22(3).
Charles M. Marson, "Targeting the Histamine H4 Receptor", Chem. Rev. 2011, 111, 7121-7156.
Dunford, P.J., et al., Hansel TT, Barnes PJ (eds): "Histamine H4 receptor antagonists", New Drugs and Targets for Asthma and COPD., Prog Respir Res. Basel, Karger 2010, vol. 39, pp. 187-191.
Fei, F., et al., "New substituted benzimidazole derivatives: a patent review (2010-2012)", Expert Opin. Ther. Patents (2013) 23(9).
Igel, P., et al., "Histamine H4 receptor agonists", Bioorganic & Medicinal Chemistry Letters, 20 (2010) 7191-7199.
Bhatt, H. G. et al., "Histamine H4 Receptor: A Novel Therapeutic Target for Immune and Allergic Responses", Mini-Reviews in Medicinal Chemistry, 2010, 10, 1293-1308.
Walter, M., et al., "Histamine receptor subtypes: a century of rational drug design", Frontiers in Bioscience S4, 461-488, Jan. 1, 2012.
Engelhardt, H. et al., "A New Generation of Anti-Histamines: Histamine H4 Receptor Antagonists on Their Way to the Clinic", Curr. Opin. Drug Disc. Dev., 2009, 12(5), 628-643.
Popov, A. et al., "Spontaneous Gelation of a Novel Histamine H4 Receptor Antagonist in Aqueous Solution", Pharm Res (2011) 28:2556-2566.
International Search Report and Written Opinion for PCT/US14/21130,(corresponding PCT Application) Jun. 6, 2014.
www.clinicaltrials.gov, "A Phase 2b Randomized, Double-blind, Placebo-controlled, Parallel Group, Dose Range Finding Study of JNJ-38518168 in Subjects with Active Rheumatoid Arthritis Despite Concomitant Methotrexate therapy", downloaded Jul. 23, 2014.
www.clinicaltrials.gov, "A Phase 2a Randomized, Double-blind, Placebo-controlled, Multicenter, Parallel Group Study of JNJ-38518168 in Adult Subjects with Uncontrolled, Persistent Asthma", downloaded Jul. 23, 2014.
Two application statements on a non-proprietary name adopted by the USAN Council dated May 28, 2014.
Róbert Kiss & György M. Keseru, "Novel Histamine H4 Receptor Ligands and Their Potential Therapeutic Applications: An Update", Expert Opinion Ther. Patents vol. 24, pp. 1185-1197, 2014.
Adachi, S. et al., "The Prevention of Postoperative Intraperitoneal Adhesions by Tranilast: N-(3',4'-dimethoxycinnamoyl) Anthranilic Acid", Surgery Today, Jpn J. Surg. (1999) 29:51-54.
Cheong, et al., "Peritoneal Healing and Adhesion Formation/Reformation," Human Reproduction Update, vol. 7, No. 6, pp. 556-566 (2001).
Shultz, et al., "New Atalysts for the Oxidation of Sulfides to Sulfones with Hydrogen Peroxide", J. Org. Chem., 1963, 28, 1140.
Stark, H. (editor), "Histamine H4 Receptor: A Novel Drug Target for Immunoregulation and Inflamation", Walter de Gruyter & Co (Dec. 2, 2013), Chapter2, Schreeb, A. et al., Histamine H4 Receptor Ligands.
Stahl et al., Handbook of Pharmaceutical Salts, Properties, Selection and Use, Eds., Wiley-VCH and VHCA, Zurich 2002.
Alberola et al., "Based-Induced Ring Cleavage of 4-Functionalized 3-Unsubstituted Isoxazoles. Synthesis of 2-Aminopyrimidines and Pyrimidine-2(3H)-Thiones", National Taiwan University Library, vol. 25, 1987, pp. 393-397.
Yu, Fuqu, et al. "Pharmacological characterization of oxime agonists of the histamine H4 receptor." J. Receptor Ligand Channel Res 3 (2010): 37-49.
Roβbach, Kristine, et al. "Histamine H4 receptor antagonism reduces hapten-induced scratching behaviour but not inflammation." Experimental dermatology 18.1 (2009): 57-63.
Leonardi, A., et al. "Histamine H4 receptors in normal conjunctiva and in vernal keratoconjunctivitis." Allergy 66.10 (2011): 1360-1366.
Massari, N. A., et al. "Role of H4 receptor in histamine-mediated responses in human melanoma." Melanoma research 21.5 (2011): 395.
Medina, V. A., et al. "Role of histamine H4 receptor in breast cancer cell proliferation." Frontiers in bioscience (Elite edition) 3 (2010): 1042-1060.
Fang, Zhengyu, et al. "Attenuated expression of HRH4 in colorectal carcinomas: a potential influence on tumor growth and progression." BMC cancer 11.1 (2011): 195.
Strakhova, Marina I., et al. "Localization of histamine H<sub>4</sub> receptors in the central nervous system of human and rat." Brain research 1250 (2009): 41-48.
Coruzzi, Gabriella, et al. "Antiinflammatory and antinociceptive effects of the selective histamine H4receptor antagonists JNJ7777120 and VUF6002 in a rat model of carrageenan-induced acute inflammation." European journal of pharmacology 563.1 (2007): 240-244.
Cowart, Marlon D., et al. "Rotationally constrained 2, 4-diamino-5, 6-disubstituted pyrimidines: a new class of histamine H4 receptor antagonists with improved druglikeness and in vivo efficacy in pain and inflammation models." Journal of medicinal chemistry 51.20 (2008): 6547-6557.
Hsieh, Gin C., et al. "H<sub>4</sub> receptor antagonism exhibits anti-nociceptive effects in inflammatory and neuropathic pain models in rats." Pharmacology Biochemistry and Behavior 95.1 (2010): 41-50.
Liu, Huaqing, et al. "cis-4-(Piperazin-1-yl)-5, 6, 7a, 8, 9, 10, 11, 11a-octahydrobenzofuro [2, 3-h] quinazolin-2-amine (A-987306), a new histamine H4R antagonist that blocks pain responses against carrageenan-induced hyperalgesia." Journal of medicinal chemistry 51.22 (2008): 7094-7098.
Krogsgaard-Larsen, Povl. A textbook of drug design and development. Harwood Academic Pub, 1991.
Alfon, et al., Inflamm. Res. 2010; 59 (Suppl 2): S199-200.
Ye, F. et al., 2014 ARVO Meeting Abstract, Program #/3291, Board #C0223, Histamine Receptor H4 as a New Therapeutic Target for Choroidal Neovascularization in Age-related macular degeneration).
Gill, D. S., C. S. Thompson, and P. Dandona. "Increased histamine in plasma and tissues in diabetic rats." Diabetes research (Edinburgh, Scotland) 7.1 (1988): 31-34.

(56) References Cited

OTHER PUBLICATIONS

Rosa, A. C., et al. "Overexpression of histamine H4 receptors in the kidney of diabetic rat." Inflammation Research 62.4 (2013): 357-365.

Bundgaard, Hans. "(C) Means to enhance penetration:(1) Prodrugs as a means to improve the delivery of peptide drugs." Advanced Drug Delivery Reviews 8.1 (1992): 1-38.

Bell, J. K., D. S. McQueen, and J. L. Rees. "Involvement of histamine H4 and H1 receptors in scratching induced by histamine receptor agonists in BalbC mice." British Journal of Pharmacology 142.2 (2004): 374-380.

Kaneko et al., "Histamine J4 receptor as a new therapeutic target for choroidal neovascularization in age-related macular degeneration", Bristish Journal of Pharmacology 171 (2014) 3754-3763.

Matsuda, N., et al., "Up-Regulation of Histamine H4 Receptors Contributes to Splenic Apoptosis in Septic Mice: Counteraction of the Antiapoptotic Action of Nuclear Factor-kB", J. Pharmacol. Exp. Ther., 2010, 332, 730-737.

Kim, Yong-Ku et al., "Cytokine imbalance in the pathophysiology of major depresseive disorder", Progress in Neuro-Psychopharmacology & Biological Psychiatry 31 (2007) 1044-1053.

Jack D. Dunitz and Joel Bernstein, "Disappearing Polymorphs", Acc. Chem. Res., 1995, vol. 28, No. 4, pp. 193-200.

John K. Haleblian and Walter Mccrone, "Pharmaceutical Applications of Polymorphism", Journal of Pharmaceutical Sciences, 1969, vol. 58, No. 8, pp. 911-929.

John K. Haleblian, "Characterization of Habits and Crystalline Modification of Solids and Their Pharmaceutical Applications", Journal of Pharmaceutical Sciences, 1975, vol. 64, No. 8, pp. 1269-1288.

BENZOIMIDAZOL-2-YL PYRIMIDINE MODULATORS OF THE HISTAMINE $H_4$ RECEPTOR

This application is a continuation of U.S. patent application Ser. No. 14/199,634, filed Mar. 6, 2014, which is incorporated herein by reference, which claims the benefit of U.S. Provisional Application 61/773,706, filed on Mar. 6, 2013, U.S. Provisional Application 61/776,260, filed on Mar. 11, 2013, and U.S. Provisional Application 61/784,909, filed on Mar. 14, 2013.

FIELD OF THE INVENTION

The present invention relates to certain benzoimidazol-2-yl pyrimidines, purification methods for the same, pharmaceutical compositions containing them, methods of obtaining and using them for the treatment of disease states, disorders, and conditions mediated by histamine $H_4$ receptor activity.

BACKGROUND OF THE INVENTION

The histamine $H_4$ receptor ($H_4R$) is one of the identified receptors for histamine (for reviews, see: Fung-Leung, W.-P., et al., Curr. Opin. Invest. Drugs 2004, 5(11), 1174-1183; de Esch, I. J. P., et al., Trends Pharmacol. Sci. 2005, 26(9), 462-469). The receptor is found in the bone marrow and spleen and is expressed on eosinophils, basophils, mast cells (Liu, C., et al., Mol. Pharmacol. 2001, 59(3), 420-426; Morse, K. L., et al., J. Pharmacol. Exp. Ther. 2001, 296(3), 1058-1066; Hofstra, C. L., et al., J. Pharmacol. Exp. Ther. 2003, 305(3), 1212-1221; Lippert, U., et al., J. Invest. Dermatol. 2004, 123(1), 116-123; Voehringer, D., et al., Immunity 2004, 20(3), 267-277), $CD8^+$ T cells (Gantner, F., et al., J. Pharmacol. Exp. Ther. 2002, 303(1), 300-307), dendritic cells, and human synovial cells from rheumatoid arthritis patients (Ikawa, Y., et al., Biol. Pharm. Bull. 2005, 28(10), 2016-2018). However, expression in neutrophils and monocytes is less well defined (Ling, P., et al., Br. J. Pharmacol. 2004, 142(1), 161-171). Receptor expression is at least in part controlled by various inflammatory stimuli (Coge, F., et al., Biochem. Biophys. Res. Commun. 2001, 284(2), 301-309; Morse, et al., 2001), thus supporting that $H_4$ receptor activation influences inflammatory responses. Because of its preferential expression on immunocompetent cells, the $H_4$ receptor is closely related with the regulatory functions of histamine during the immune response.

A biological activity of histamine in the context of immunology and autoimmune diseases is closely related with the allergic response and its deleterious effects, such as inflammation. Events that elicit the inflammatory response include physical stimulation (including trauma), chemical stimulation, infection, and invasion by a foreign body. The inflammatory response is characterized by pain, increased temperature, redness, swelling, reduced function, or a combination of these.

Mast cell degranulation (exocytosis) releases histamine and leads to an inflammatory response that may be initially characterized by a histamine-modulated wheal and flare reaction. A wide variety of immunological stimuli (e.g., allergens or antibodies) and non-immunological (e.g., chemical) stimuli may cause the activation, recruitment, and de-granulation of mast cells. Mast cell activation initiates allergic inflammatory responses, which in turn cause the recruitment of other effector cells that further contribute to the inflammatory response. It has been shown that histamine induces chemotaxis of mouse mast cells (Hofstra, et al., 2003). Chemotaxis does not occur using mast cells derived from $H_4$ receptor knockout mice. Furthermore, the response is blocked by an $H_4$-specific antagonist, but not by $H_1$, $H_2$ or $H_3$ receptor antagonists (Hofstra, et al., 2003; Thurmond, R. L., et al., J. Pharmacol. Exp. Ther. 2004, 309(1), 404-413). The in vivo migration of mast cells to histamine has also been investigated and shown to be $H_4$ receptor dependent (Thurmond, et al., 2004). The migration of mast cells may play a role in allergic rhinitis and allergy where increases in mast cell number are found (Kirby, J. G., et al., Am. Rev. Respir. Dis. 1987, 136(2), 379-383; Crimi, E., et al., Am. Rev. Respir. Dis. 1991, 144(6), 1282-1286; Amin, K., et al., Am. J. Resp. Crit. Care Med. 2000, 162(6), 2295-2301; Gauvreau, G. M., et al., Am. J. Resp. Crit. Care Med. 2000, 161(5), 1473-1478; Kassel, O., et al., Clin. Exp. Allergy 2001, 31(9), 1432-1440). In addition, it is known that in response to allergens there is a redistribution of mast cells to the epithelial lining of the nasal mucosa (Fokkens, W. J., et al., Clin. Exp. Allergy 1992, 22(7), 701-710; Slater, A., et al., J. Laryngol. Otol. 1996, 110, 929-933). These results show that the chemotactic response of mast cells is mediated by histamine $H_4$ receptors.

It has been shown that eosinophils can chemotax towards histamine (O'Reilly, M., et al., J. Recept. Signal Transduction 2002, 22(1-4), 431-448; Buckland, K. F., et al., Br. J. Pharmacol. 2003, 140(6), 1117-1127; Ling et al., 2004). Using $H_4$ selective ligands, it has been shown that histamine-induced chemotaxis of eosinophils is mediated through the $H_4$ receptor (Buckland, et al., 2003; Ling et al., 2004). Cell surface expression of adhesion molecules CD11b/CD18 (LFA-1) and CD54 (ICAM-1) on eosinophils increases after histamine treatment (Ling, et al., 2004). This increase is blocked by $H_4$ receptor antagonists but not by $H_1$, $H_2$, or $H_3$ receptor antagonists.

The $H_4R$ also plays a role in dendritic cells and T cells. In human monocyte-derived dendritic cells, $H_4R$ stimulation suppresses IL-12p70 production and drives histamine-mediated chemotaxis (Gutzmer, R., et al., J. Immunol. 2005, 174 (9), 5224-5232). A role for the $H_4$ receptor in $CD8^+$ T cells has also been reported. Gantner, et al., (2002) showed that both $H_4$ and $H_2$ receptors control histamine-induced IL-16 release from human $CD8^+$ T cells. IL-16 is found in the bronchoalveolar fluid of allergen- or histamine-challenged asthmatics (Mashikian, V. M., et al., J. Allergy Clin. Immunol. 1998, 101 (6, Part 1), 786-792; Krug, N., et al., Am. J. Resp. Crit. Care Med. 2000, 162(1), 105-111) and is considered important in CD4 cell migration. The activity of the receptor in these cell types indicates an important role in adaptive immune responses such as those active in autoimmune diseases.

In vivo $H_4$ receptor antagonists were able to block neutrophillia in zymosan-induced peritonitis or pleurisy models (Takeshita, K., et al., J. Pharmacol. Exp. Ther. 2003, 307(3), 1072-1078; Thurmond, R., et al., 2004). In addition, $H_4$ receptor antagonists have activity in a widely used and well-characterized model of colitis (Varga, C., et al., Eur. J. Pharmacol. 2005, 522(1-3), 130-138). These results support the conclusion that $H_4$ receptor antagonists have the capacity to be anti-inflammatory in vivo.

Another physiological role of histamine is as a mediator of itch and $H_1$ receptor antagonists are not completely effective in the clinic. Recently, the $H_4$ receptor has also been implicated in histamine-induced scratching in mice (Bell, J. K., et al., Br. J. Pharmacol. 2004, 142(2), 374-380). The effects of histamine could be blocked by $H_4$ antagonists. These results support the hypothesis that the $H_4$ receptor is involved in histamine-induced itch and that $H_4$ receptor antagonists will therefore have positive effects in treating pruritus.

Modulation of $H_4$ receptors controls the release of inflammatory mediators and inhibits leukocyte recruitment, thus providing the ability to prevent and/or treat $H_4$-mediated diseases and conditions, including the deleterious effects of allergic responses such as inflammation. Compounds according to the present invention have $H_4$ receptor modulating properties. Compounds according to the present invention have leukocyte recruitment inhibiting properties. Compounds according to the present invention have anti-inflammatory properties.

Examples of textbooks on the subject of inflammation include: Gallin, J. I.; Snyderman, R., *Inflammation: Basic Principles and Clinical Correlates,* 3rd ed.; Lippincott Williams & Wilkins: Philadelphia, 1999; Stvrtinova, V., et al., Inflammation and Fever. *Pathophysiology Principles of Diseases* (Textbook for Medical Students); Academic Press: New York, 1995; Cecil; et al. *Textbook Of Medicine,* 18th ed.; W.B. Saunders Co., 1988; and Stedman's Medical Dictionary.

Background and review material on inflammation and conditions related with inflammation can be found in articles such as the following: Nathan, C., Nature 2002, 420(6917), 846-852; Tracey, K. J., Nature 2002, 420(6917), 853-859; Coussens, L. M., et al., Nature 2002, 420(6917), 860-867; Libby, P., Nature 2002, 420, 868-874; Benoist, C., et al., Nature 2002, 420(6917), 875-878; Weiner, H. L., et al., Nature 2002, 420(6917), 879-884; Cohen, J., Nature 2002, 420(6917), 885-891; Steinberg, D., Nature Med. 2002, 8(11), 1211-1217.

Thus, small-molecule histamine $H_4$ receptor modulators according to this invention control the release of inflammatory mediators and inhibit leukocyte recruitment, and may be useful in treating inflammation of various etiologies, including the following conditions and diseases: inflammatory disorders, allergic disorders, dermatological disorders, autoimmune disease, lymphatic disorders, pruritus, and immunodeficiency disorders. Diseases, disorders and medical conditions that are mediated by histamine $H_4$ receptor activity include those referred to herein.

Histamine $H_4$ receptor modulators have been described in, for example: U.S. Pat. No. 7,432,378; U.S. Pat. No. 7,507,737; U.S. Pat. No. 8,343,989; U.S. Pat. Appl. Publ. 2009/0137608; U.S. patent application Ser. No. 13/676,595 (U.S. Pat. No. 8,598,189); U.S. Pat. No. 8,309,720; U.S. patent application Ser. No. 13/663,233; and U.S. Pat. Appl. Publ. 2011/0076324, all of which are incorporated by reference herein. Histamine $H_4$ receptor moduators have also been described in, for example, U.S. Pat. Appl. Publ. 2010/0029942; U.S. Pat. Appl. Publ. 2012/0184740; U.S. Pat. Appl. Publ. 2012/0178932, and WO2010/002777. However, there still remains a need for histamine $H_4$ receptor modulators with desirable pharmaceutical properties.

As to specific forms of such modulators, active pharmaceutical ingredients that are initially in free base form are often converted into their salt forms to improve certain of their pharmaceutical properties. There is typically a plurality of salts that can be made from a sufficiently basic compound, as is the case with compounds described in this application. As to specific salts, a specific solvate of the same, if any, and of such, the specific degree of solvation that will lead to a certain desired improvement of pharmaceutical properties, are often unpredictable. This has been recognized in, for example, WO2012/060590, which states, inter alia, that "there is no general tendency, for example, to prefer the hydrate to the anhydrate or vice versa, for the improvement of pharmaceutical properties including drug stability, hygroscopic property, etc.", and that optimization of pharmaceutical properties is to be made on a case-by-case basis. Physical pharmaceutical properties, such as hygroscopicity, crystallinity, melting point, solubility, dissolution rate, and impurity segregation ability, can present predictability challenges. Furthermore, identifying a specific form of an active pharmaceutical compound that optimally presents such properties for desirable formulations of the same compound can be in certan instances difficult to accomplish. Because of these limitations in what one of ordinary skill in the art would be able to expect regarding such properties, and the role that they play in certain aspects of the pharmaceutical industry, there still remains a need for finding specific forms of certain pharmaceutical compounds with improved properties, such as those illustratively listed above.

SUMMARY OF THE INVENTION

This invention relates to a hydrated hemitartrate benzoimidazol-2-yl pyrimidine as shown by the following structural formula and methods of using, obtaining and purifying the same.

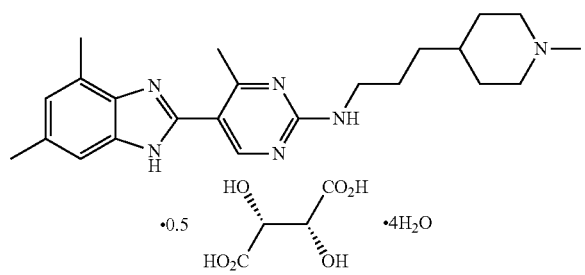

This invention also relates to a fumarate and a phosphate of the same benzoimidazol-2-yl pyrimidine.

In a further aspect, the invention relates to pharmaceutical compositions each comprising an effective amount of at least one of the above compounds.

In another aspect, the invention is directed to a method of treating a subject suffering from or diagnosed with a disease, disorder, or medical condition mediated by histamine $H_4$ receptor activity, comprising administering to the subject in need of such treatment an effective amount of at least one of the above compounds or a pharmaceutically acceptable salt thereof, pharmaceutically acceptable prodrug, or pharmaceutically active metabolite of such compounds. In certain preferred embodiments of the inventive method, the disease, disorder, or medical condition is inflammation. Inflammation herein refers to the response that develops as a consequence of histamine release, which in turn is caused by at least one stimulus. Examples of such stimuli are immunological stimuli and non-immunological stimuli.

In another aspect, the invention is directed to a method for modulating histamine $H_4$ receptor activity, comprising exposing a histamine $H_4$ receptor to an effective amount of at least one of the above compounds.

In another aspect the invention is directed to the making, including purifying the above compounds.

Additional embodiments, features, and advantages of the invention will be apparent from the following detailed description and through practice of the invention.

DETAILED DESCRIPTION OF THE INVENTION

Figure 1:
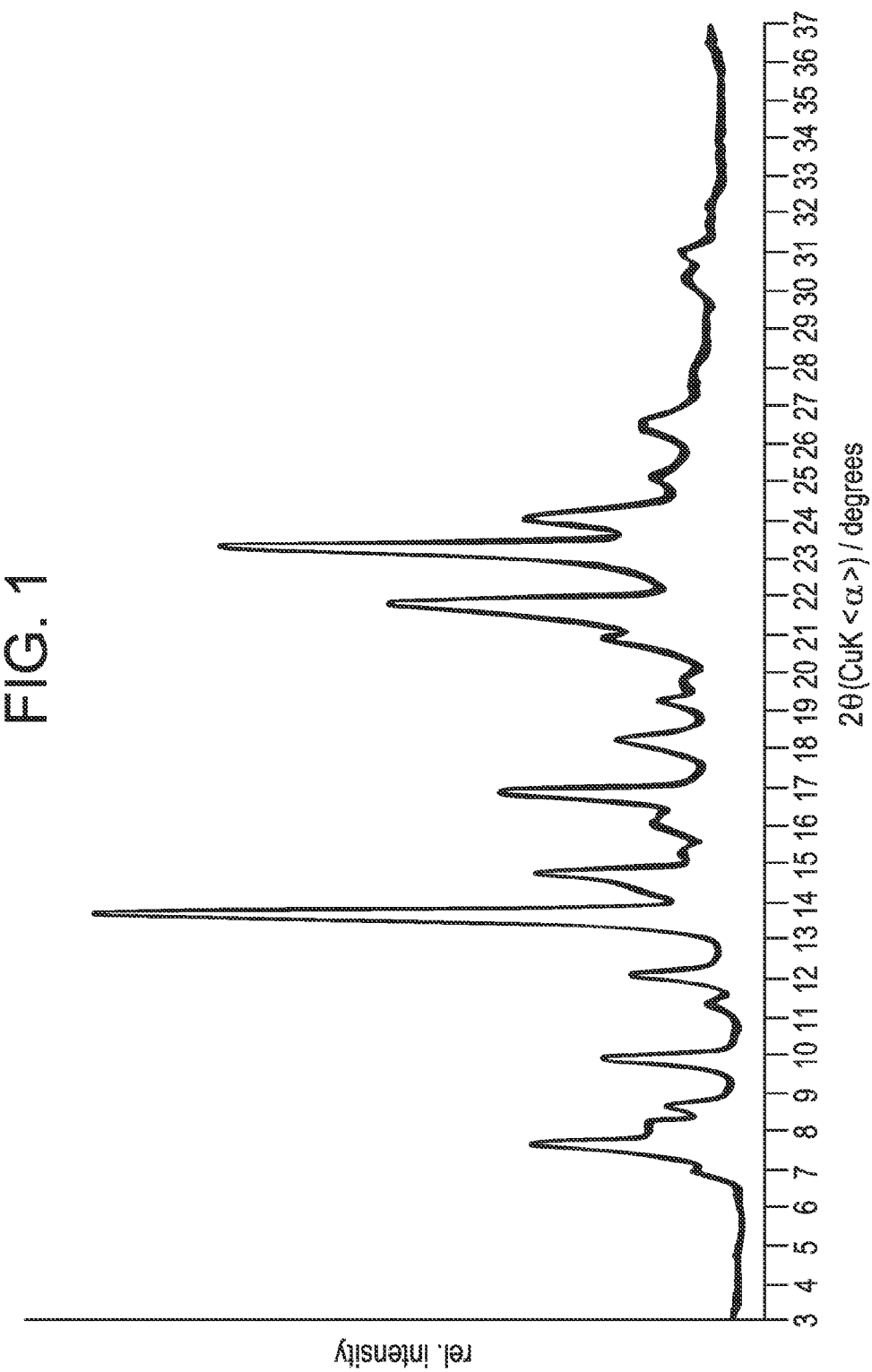
FIG. 1. Powder X-ray diffraction (XRD) profile of Compound 2.2

As used herein, the terms "including", "containing" and "comprising" are used in their open, non-limiting sense.

Unless qualified specifically in particular instances of use, the term "low alkyl" or "low-alkyl" refers to a straight- or branched-chain alkyl group having from 1 to 6 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. "$C_{1-4}$alkyl" refers to straight- or branched-chain alkyl group having from 1 to 4 carbon atoms in the chain.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once in the same formula, the choice of the species from a specified list is independent of the choice of the species for the same variable elsewhere in the formula, unless stated otherwise.

Compound 2 has $H_4$ receptor modulator activity as described in, for example U.S. Pat. No. 7,507,737, U.S. Pat. No. 8,343,989, U.S. Application Publ. US2009/0137608 and U.S. application Ser. No. 13/676,595 (U.S. Pat. No. 8,598,189), all of which are incorporated herein by reference:

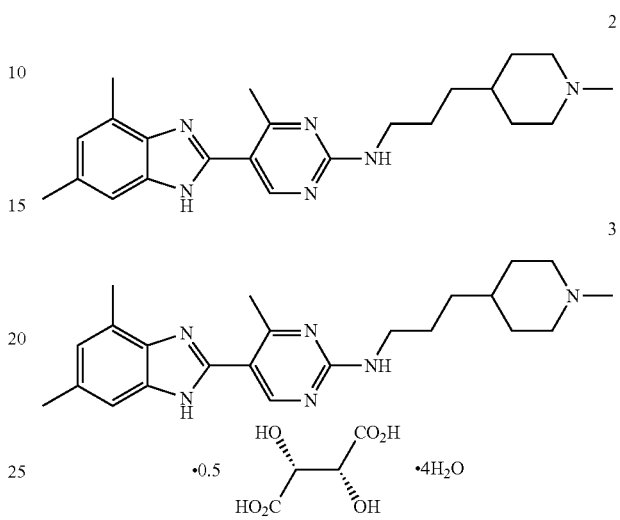

It has been found in the context of this invention that the hemitartrate tetrahydrate of Compound 2, referred to herein as Compound 3, has improved desirable physical pharmaceutical properties, which make of it an even more suitable chemical entity for the prevention or treatment of medical conditions, diseases or disorders mediated by $H_4$ receptor activity. Impurities in pharmaceuticals are unwanted chemicals that remain with the active pharmaceutical ingredients after their synthesis, develop during formulation, or when active pharmaceutical ingredients, whether formulated as medicines or not, are aged to medicines. The control of pharmaceutical impurities is an important issue to the pharmaceutical industry. It has been discovered that Compound 3 has impurity segregation properties that confer to it improved physical pharmaceutical properties because its synthesis permits the more efficient removal of impurities and/or the removal of impurities to an exent such that otherwise would require more laborious purification processes.

Compound 3 can be administered to treat inflammation. Inflammation may be associated with various diseases, disorders, or conditions, such as inflammatory disorders, allergic disorders, dermatological disorders, autoimmune disease, lymphatic disorders, and immunodeficiency disorders, including the more specific conditions and diseases given below. Regarding the onset and evolution of inflammation, inflammatory diseases or inflammation-mediated diseases or conditions include, but are not limited to, acute inflammation, allergic inflammation, and chronic inflammation.

Illustrative types of inflammation treatable with a histamine $H_4$ receptor-modulating agent according to the invention include inflammation due to or associated with any one of a plurality of conditions such as allergy, asthma, eosinophilic asthma, dry eye, chronic obstructive pulmonary disease (COPD), atherosclerosis, rheumatoid arthritis, multiple sclerosis, inflammatory bowel diseases (including colitis, Crohn's disease, and ulcerative colitis), psoriasis, pruritus, itchy skin, atopic dermatitis, urticaria (also known as hives), ocular inflammation, conjunctivitis, nasal polyps, allergic rhinitis, nasal itch, parasitic or fungal infections (e.g., lice, scabies, swimmer's itch, jock itch, athlete's foot), hidradenitis suppurativa, malignancy, such as lymphoma (e.g., Hodgkin's disease), jaundice, polycythemia, punctate palmoplantar keratoderma, thyroid illness/hyperparathyroidism, diabetes, chicken pox, iron deficiency anemia, psychiatric diseases, medication-induced itch (e.g., allergies, photodermatitis, morphine, opiates, chloroquine); cholestasis; pregnancy-related itch (e.g., obstetric cholestasis, pruritic urticaria papules and plaques of pregnancy, gestational pemphigoid); xerosis (also known as dry skin), sunburn, dandruff, scab/scars, insect bites, poison ivy/oak, hemorrhoids, contact dermatitis, old-age associated itch, itch associated with dialysis, scleroderma, autoimmune thyroid diseases, immune-mediated (also known as type 1) diabetes mellitus and lupus, which are characterized by excessive or prolonged inflammation at some stage of the disease. Other autoimmune diseases that lead to inflammation include Myasthenia gravis, autoimmune neuropathies, such as Guillain-Barré, autoimmune uveitis, autoimmune hemolytic anemia, pernicious anemia, autoimmune thrombocytopenia, temporal arteritis, anti-phospholipid syndrome, vasculitides, such as Wegener's granulomatosis, Behcet's disease, dermatitis herpetiformis, pemphigus vulgaris, vitiligio, primary biliary cirrhosis, autoimmune hepatitis, autoimmune oophoritis and orchitis, autoimmune disease of the adrenal gland, polymyositis, dermatomyositis, spondyloarthropathies, such as ankylosing spondylitis, Sjogren's syndrome and pruritus.

Pruritus includes that which is a symptom of allergic cutaneous diseases (such as atopic dermatitis and hives) and other metabolic disorders (such as chronic renal failure, hepatic cholestasis, and diabetes mellitus).

Compound 3 can also be administered to treat mood disorders (including but not limited to major depressive disorder, bipolar disorder, treatment resistant major depressive disorder and treatment resistant bipolar disorder), anxiety disorders (including but not limited to generalized anxiety disorder, social phobia, and post traumatic stress disorder).

Compound 3 may also be administered with a long acting β-agonist, acting in a synergistic manner to improve lung finctions and asthma in the treatment of asthma.

In another embodiment, Compound 3 is administered to treat allergy, asthma, autoimmune diseases, or pruritus.

The term "treat" or "treating" as used herein is intended to refer to administration of Compound 3 to a subject for the purpose of effecting a therapeutic or prophylactic benefit through modulation of histamine $H_4$ receptor activity. Treating includes reversing, ameliorating, alleviating, inhibiting the progress of, lessening the severity of, or preventing a disease, disorder, or condition, or one or more symptoms of such disease, disorder or condition mediated through modulation of histamine $H_4$ receptor activity. The term "subject" refers to a mammalian patient in need of such treatment, such as a human. "Modulators" include both inhibitors and activators, where "inhibitors" refer to compounds that decrease, prevent, inactivate, desensitize or down-regulate histamine $H_4$ receptor expression or activity, and "activators" are compounds that increase, activate, facilitate, sensitize, or up-regulate histamine $H_4$ receptor expression or activity.

In treatment methods according to the invention, an effective amount of at least Compound 3 is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of Compound 3 may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An example of a dose is in the range of from about 0.001 to about 200 mg of free base equivalent per kg of subject's body weight per day, preferably about 0.01 to 7 mg/kg/day, most preferably about 0.04 to 1.4 mg/kg/day, in single or divided dosage units (e.g., twice a day, three times a day, four times a day). For a 70-kg human, an illustrative range for a suitable oral dosage amount of free base equivalent is from about 0.05 to about 300 mg/day, or preferably about 1 to 50 mg/day, more preferably from about 3 to 30 mg/day, most preferably a dose of 3 mg/day or 10 mg/day or 30 mg/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, Compound 3 may be used in combination with additional active compounds in the treatment of the above conditions. The additional compounds may be coadministered separately with Compound 3 or included with such an agent as an additional active ingredient in a pharmaceutical composition according to the invention. In an illustrative embodiment, additional active compounds are those that are known or discovered to be effective in the treatment of conditions, disorders, or diseases mediated by histamine $H_4$ receptor activity, such as another histamine $H_4$ receptor modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the agent according to the invention.

When referring to modulating the target receptor, an "effective amount" means an amount sufficient to affect the activity of such receptor. Measuring the activity of the target receptor may be performed by routine analytical methods. Target receptor modulation is useful in a variety of settings, including assays.

Compound 3 is used, alone or in combination with one or more other active ingredients, to formulate pharmaceutical compositions of the invention. A pharmaceutical composition of the invention comprises an effective amount of at least Compound 3. A pharmaceutically acceptable excipient is part of some embodiments of pharmaceutical compositions according to this invention.

A "pharmaceutically acceptable excipient" refers to a substance that is not toxic, but it is biologically tolerable, or otherwise biologically suitable for administration to a subject, such as an inert substance, added to a pharmacological composition or otherwise used as a vehicle, carrier, or diluent to facilitate administration of a pharmaceutical agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of Compound 3 may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, Compound 3 of the invention can be provided in the form of tablets or capsules, or as a solution, emulsion, or suspension. To prepare the oral compositions, Compound 3 may be formulated to yield an amount of free base equivalent dosage of, e.g., from about 0.05 to about 50 mg/kg daily, or from about 0.05 to about 20 mg/kg daily, or from about 0.1 to about 10 mg/kg daily, most preferably 3 mg/day, 10 mg/day or 30 mg/day.

Oral tablets may include the agent and any other active ingredients mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Examples of liquid oral excipients include ethanol, glycerol, water, and the like. Starch, polyvinyl-pyrrolidone (PVP), sodium starch glycolate, microcrystalline cellulose, and alginic acid are examples of disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

In some embodiments of the invention, tablets are in the form of coated tablets, and they contain Compound 3 tabletted with a filler/binder, that in some embodiments is silicified microcrystalline cellulose or colloidal silicon dioxide in amounts ranging from about 65.5 mg/tablet to about 190.4 mg/tablet, a filler that in some embodiments is mannitol in amounts ranging from about 21.0 mg/tablet to about 63 mg/tablet, a glidant, that in some embodiments is silica colloidal anhydrous in amounts ranging from about 0.3 mg/tablet to about 0.9 mg/tablet, a lubricant that in some embodiments is magnesium stearate in amounts ranging from about 1.5 mg/tablet to about 4.5 mg/tablet, and a film coating agent, that in some embodiments is opadry white II 85F18422 in amounts ranging from about 3.0 mg/tablet to about 9.0 mg/tablet. Amounts of Compound 3 in embodiments of such tablets are 4.124 mg, 13.747 mg, and 41.241 mg, or amounts that correspond to free base equivalent amounts of 3 mg, 10 mg, and 30 mg.

Capsules for oral administration include hard and soft gelatin capsules. To prepare hard gelatin capsules, active ingredient may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

Compound 3 may also be administered by non-oral routes. For example, the compositions may be formulated for rectal administration as a suppository. For parenteral use, including intravenous, intramuscular, intraperitoneal, or subcutaneous routes, Compound 3 may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent, admixed with a pharmaceutical carrier over a period ranging from several minutes to several days.

For topical administration, the Compound 3 may be mixed with a pharmaceutical carrier at a concentration of about 0.1% to about 10% of drug to vehicle. Another mode of administering Compound 3 may utilize a patch formulation to affect transdermal delivery.

Administration of Compound 3 according to methods of this invention may be made by inhalation, via the nasal or oral routes, e.g., in a spray formulation also containing a suitable carrier.

It is envisaged that Compounds 4 and 5 can also be administered as Compounds 3, 2.1 and 2.2 according to methods of use of this invention.

Examples of chemical entities useful in methods of the invention will now be described by reference to illustrative synthetic schemes for their general preparation below and the specific examples that follow. Those of ordinary skill in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent.

In the Schemes depicted below, one of ordinary skill in the art will recognize that $R^6$ may be H or a suitable nitrogen protecting group, such as a tert-butoxycarbonyl group (Boc), and that protecting group replaced at a later stage in the synthesis.

SCHEME A

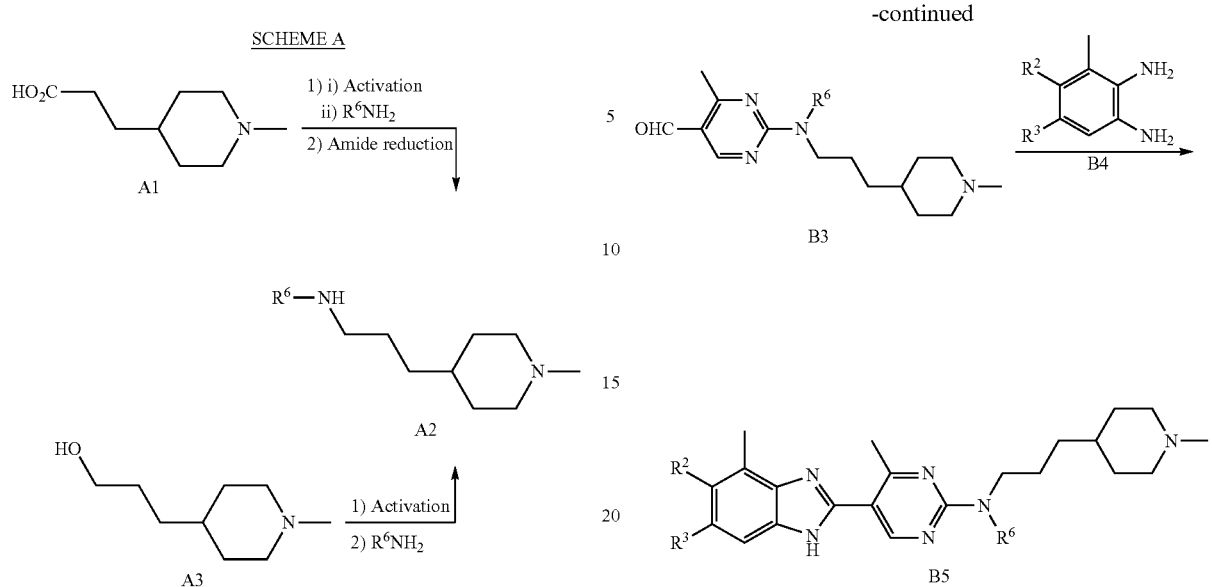

Referring to Scheme A, amines A2 are commercially available or are prepared from acids A1 or alcohols A3. Coupling of acids A1 with amines $R^6NH_2$, in the presence of activating agents such as dicyclohexyl-carbodiimide, EDC/HOBt, or carbonyl diimidazole, in a solvent such as DMF or THF, provides the corresponding amides (not shown). Alternatively, acids A1 are activated to their corresponding acid chlorides and reacted with amines $R^6NH_2$ in the presence of a suitable base such as triethylamine or diisopropylethylamine, in a solvent such as DCM or THF. The resulting amides are reduced to amines A2 by a suitable reducing agent such as $LiAlH_4$, in a solvent such as THF. Alcohols A3 are activated using general methods to form, for example, alkyl halides or alkyl tosylates. Displacement with $R^6NH_2$ in the presence of a suitable base such as NaH, NaOH, triethylamine, or diisopropylethylamine, in a solvent such as DCM or THF, provides amines A2. Alternatively, amines A2 are prepared from alcohols A3 by reaction with phthalimide or a suitable amino surrogate under Mitsunobu conditions. Where phthalimide is used, the free amine is revealed through treatment with hydrazine.

Referring to Scheme B, amines A2 are reacted with pyrimidines B1, which are commercially available or are prepared by oxidation of commercially available alkylsulfanyl pyrimidines, or by other general methods, in a solvent such as pyridine, DMF, MeOH, or EtOH, or a mixture thereof, at temperatures between about room temperature and the reflux temperature of the solvent, or in a sealed tube at temperatures up to about 120° C. In B4 and B5, $R^2$ may be H or F and $R^3$ may be $CH_3$ or H. 2-Aminopyrimidines B2 are converted to aldehydes B3 by reduction of the Y substituent with a suitable reducing agent such as diisobutylaluminum hydride. Where Y is an ester group, reduction produces aldehydes B3 or the corresponding alcohols (not shown). Where an alcohol is produced, oxidation using a suitable oxidizing agent such as $MnO_2$, Dess-Martin periodinane, or Swern conditions, provides aldehydes B3. Condensation of aldehydes B3 with suitably substituted diamines B4, in the presence of a dehydrating agent such as $NaH_2S_2O_5$, in a solvent such as DMF, MeOH, or EtOH, or a mixture thereof, at temperatures between about room temperature and the reflux temperature of the solvent, produces compounds of Formula B5.

SCHEME B

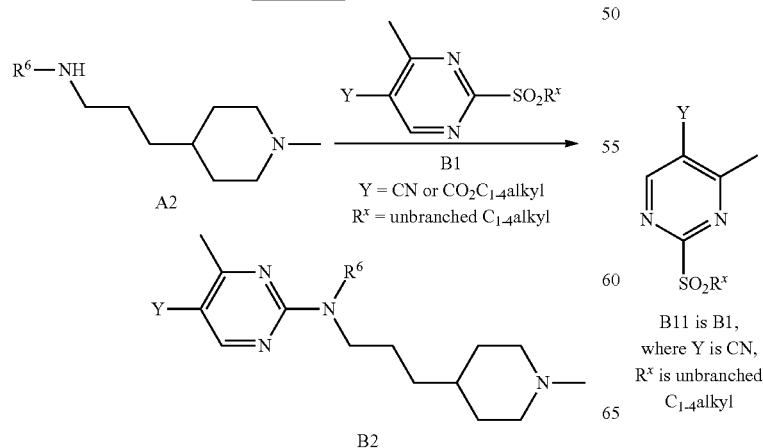

SCHEME B.1

1. Toluene/water
2.

A21 where $R^6$ is H
as solution in aq. $K_2CO_3$/20-30° C.
3. about 60° C., phase separation
4. wash with aq. NaOH, phase separation
5. wash with $H_2O$, phase separation
6. dist. of toluene
7. crystallization B11 is B1, where Y is CN, $R^x$ is unbranched $C_{1-4}$alkyl

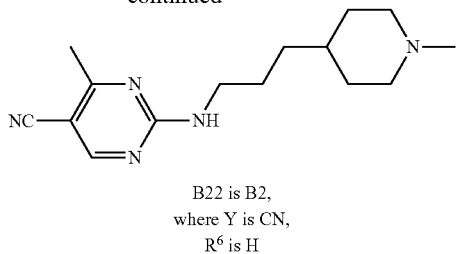

B22 is B2,
where Y is CN,
R[6] is H

In addition to synthetic methodologies for preparing compound B22 as described in Scheme B, other methodologies have been described in, for example, US patent application publication US2010/0004450, U.S. Pat. No. 8,309,720, which is incorporated by reference herein in its entirety. For illustrative nonlimiting purposes, see examples 7, 10, 12, 16, 24 and 25 in such publication. An alternative procedure for the preparation of B22, employs compounds A21 and B11 in a bi-phasic solvent system such as toluene and water along with a base such as $K_2CO_3$ with heating to a temperature of about 60-65° C. as shown in Scheme B.1. In an embodiment of this reaction, compound A21 in an aqueous solution of 10% $K_2CO_3$ is added to a solution of B11 in a solvent such as toluene. The reaction mixture of A21 and B11 is heated to a temperature between 60° C. and 65° C. In a subsequent step, after heating for approximately 20 min at a temperature between 60-65° C., the aqueous portion is removed, a solution of 1N $NaOH_{(aq)}$ is added and heated to temperature between 60-65° C. for approximately 10 minutes. The $NaOH_{(aq)}$ solution is removed and water added and heated to a temperature between 60-65° C. for approximately 10 minutes. In a subsequent step, the water solution is removed and the remaining organic solvent is removed by distillation. Compound B22 is optionally purified by recrystallization from a solvent such as toluene.

Scheme B.2

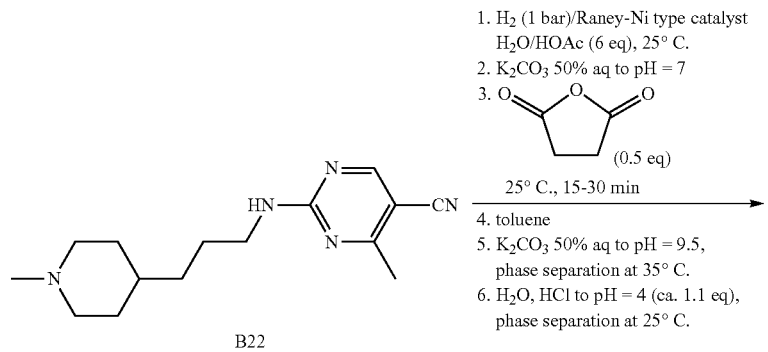

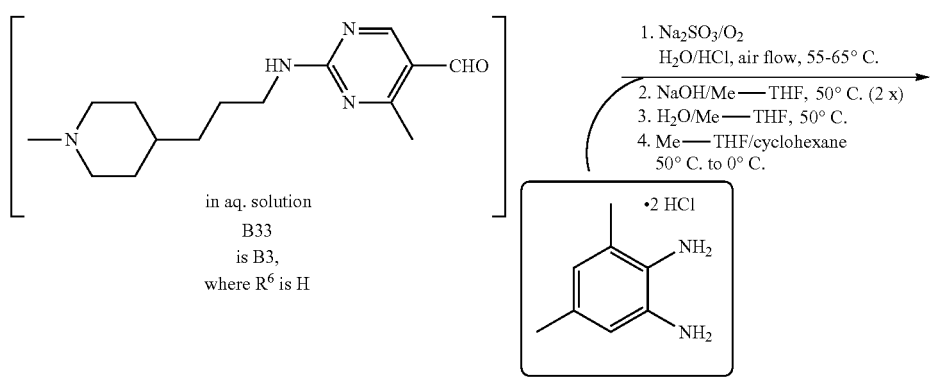

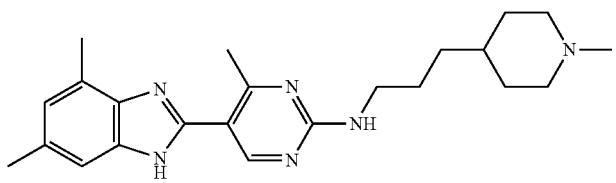

An alternative procedure for performing Scheme B is outlined in Scheme B.2. Compound B33 according to this scheme is not isolated. The methodology according to this scheme employs compound B22, a catalyst which is a fine grained solid composed mostly of nickel derived from a nickel-aluminum alloy, such as Raney nickel, and hydrogen gas in a solvent such as aqueous acetic acid at a temperature between 20-40° C. Embodiments of this methodology use substoichiometric amounts of such catalyst. This is an advantageous feature, for the presence of a stoichiometric amount of catalyst is not a determining feature in this methodology. Many processes that use the same catalyst rely on its presence in stoichiometric amounts of such catalyst. Another feature of this methodology is the use of succinic anhydride, which permits a substantial removal of impurity I1. Compound B22 is reduced by hydrogenation with a catalyst as indicated above. When such hydrogenation is complete, as judged by there being less than about 3% of compound B22 remaining, the catalyst is removed by filtration and the filtrate neutralized to pH=7 with an aqueous $K_2CO_3$ solution (50% w/w). Subsequently, succinic anhydride is added, and an organic solvent, such as toluene for example, is added. A bi-phasic organic-aqueous medium is thus formed. In an envisaged alternative embodiment that would also lead to a bi-phasic organic-aqueous medium, succinic anhydride is dissolved in an organic sovent, which then is added to the aqueous medium. Such anhydride derivatizes an impurity. In a subsequent step, the pH of the solution is adjusted to about 9.5 with an appropriate base. In some embodiments such pH adjustment was performed with an aqueous $K_2CO_3$ solution (50% w/w) followed by heating to a temperature of about 35° C. for approximately 15-30 minutes. Phase-separation of the organic layer is performed afterwards. The organic portion of the reaction mixture is collected, the aqueous portion is optionally re-extracted with a solvent such as toluene, and the organic portion resulting from the second extraction, when such second extraction is performed, is combined with the first organic portion. In a subsequent step the organic portion is cooled to a temperature between 15-25° C. and the pH adjusted to about 3.5-4 with an appropriate acid. In some embodiments, such pH adjustment was performed by the addition of an 8% aqueous HCl solution. In a subsequent step, the organic and aqueous portions are separated, and the aqueous portion contains compound B33.

In a separate vessel, sodium sulfite, 1,2-diamino-3,5-dimethylbenzene dihydrochloride and water are stirred at room temperature. Hydrochloric acid is added and the reaction is heated to 50° C. within 20 minutes. Air flow is circulated through the solution. Compound B33 in aqueous solution, is added to this medium over 1.5 h to form a reaction mixture that contains the reaction product of compound B33 and the diamino-dimethylbenzene. The reaction mixture is heated to a temperature of about 55-60° C. for approximately 1-2.5 h. In a subsequent step, the solids are filtered off and 2-methyltetrahydrofuran is added to the filtrate. In a subsequent step, 30% $NaOH_{(aq)}$ is added to adjust the pH to approximately 9.5-11.5. The reaction mixture is heated to 45-50° C. for 15 min. A series of extraction steps are performed afterwards. The aqueous layer is removed and discarded, and water and 30% $NaOH_{(aq)}$ are added to the organic layer, thus forming a bi-phasic medium, which is heated to 45-50° C. for 5-15 min. The aqueous layer from this bi-phasic medium is removed and discarded, and water is added to the remaining organic layer, thus forming another bi-phasic medium, which is then heated to 45-50° C. for 5-15 min. The aqueous layer from such medium is removed and discarded, and cyclohexane added and the organic layer, which is heated to 45-50° C., and then solid Compound 2 is obtained by cooling such organic layer to 0-5° C., out of which Compound 2 crystallizes and is isolated by filtration.

SCHEME C

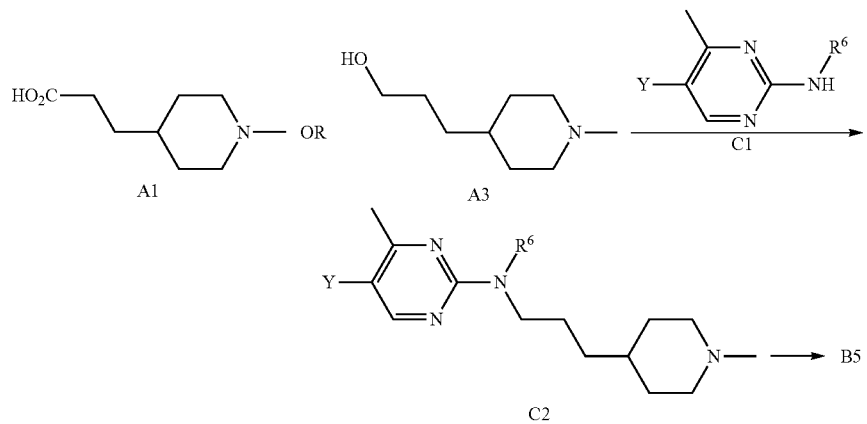

Referring to Scheme C, acids A1 or alcohols A3 may be coupled with 2-aminopyrimidines C1 using the methods described in Scheme A to form amides (not shown) and amines C2. The amides and compounds C2 are processed as described in Scheme B to provide compounds of Formula B5.

Additional synthetic methods are described in U.S. Pat. Nos. 7,507,737 and 8,309,720, which are hereby incorporated by reference. Additional synthetic methods are described in U.S. Pat. Appl. Publ. 2010/0029942.

Additional synthetic methods can be designed from the description provided in U.S. Pat. Appl. Publ. 2005/0070550 (U.S. Pat. No. 7,432,378), which is hereby incorporated by reference.

The following examples are provided to further illustrate aspects of the invention and various preferred embodiments.

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions are "dried," they are generally dried over a drying agent such as Na$_2$SO$_4$ or MgSO$_4$. Where mixtures, solutions, and extracts were "concentrated", they were typically concentrated on a rotary evaporator under reduced pressure.

Thin-layer chromatography was performed using Merck silica gel 60 F$_{254}$ 2.5 cm×7.5 cm, 250 μm or 5.0 cm×10.0 cm, 250 μm pre-coated silica gel plates.

Normal-phase flash column chromatography (FCC) was performed on silica gel (SiO$_2$) eluting with 2 M NH$_3$ in MeOH/DCM, unless otherwise noted.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1$H NMR data below is: chemical shift in ppm downfield of the tetramethylsilane reference (multiplicity, coupling constant J in Hz, integration).

Powder X-ray diffraction characterizations of compounds exemplied herein were performed by using a variety of X ray sources and diffractometers as indicated below.

Powder X-ray diffraction profiles and associated data of compound 2.2, which are shown in FIG. 1, and whose data are presented in Tables 2 and 2.1, were performed on an APD 2000 Diffraktometer (G.N.R. s.r.l., Agrate Conturbia, Italy) equipped with a NaI scintillation counter. Samples were scanned from 3° to 40° 2θ at a step size of 0.01° and a time per step of 5 seconds. The tube voltage and current were 40 kV and 30 mA, respectively. The samples were placed onto zero background aluminum holders.

Figure 4:
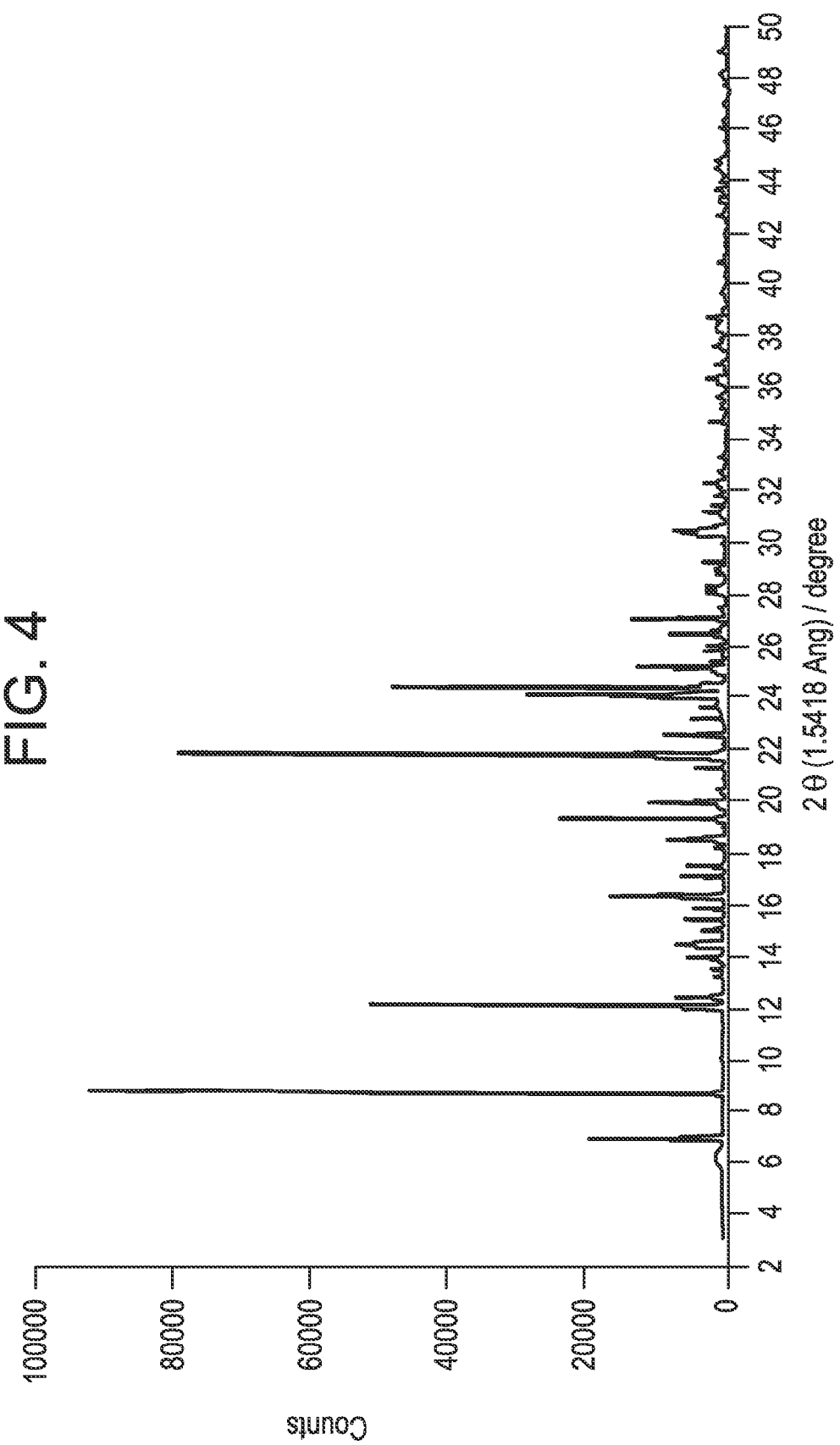
FIG. 4. XRD profile of Compound 3

Synchrotron powder X-ray diffraction measurements and associated data of compound 3, which are shown in FIG. 4 and whose data are presented in Tables 5, 6, 6.1, 6.2 and 6.3, were performed at the Materials Science beam line of the Swiss Light Source (SLS) at the Paul Scherrer Institute (PSI) in Villigen (Switzerland). Samples were measured in spinning glass capillaries with a diameter of 1.0 mm at T=295K. The wavelength of the radiation used for the experiment was determined from a silicon powder measurement and refinement: λ=(1.000180±0.000051) Å, energy=(12.395773±0.000627) keV, 2θ offset=(+0.001474±0.000032)°; detector: micro strip; temperature control: cryojet; a robot system was used for mounting the capillaries. The recorded powder profiles were pre-processed at the PSI and then transformed to the CuK<α> wavelength scale (λ=1.5418 Å).

Figure 9:
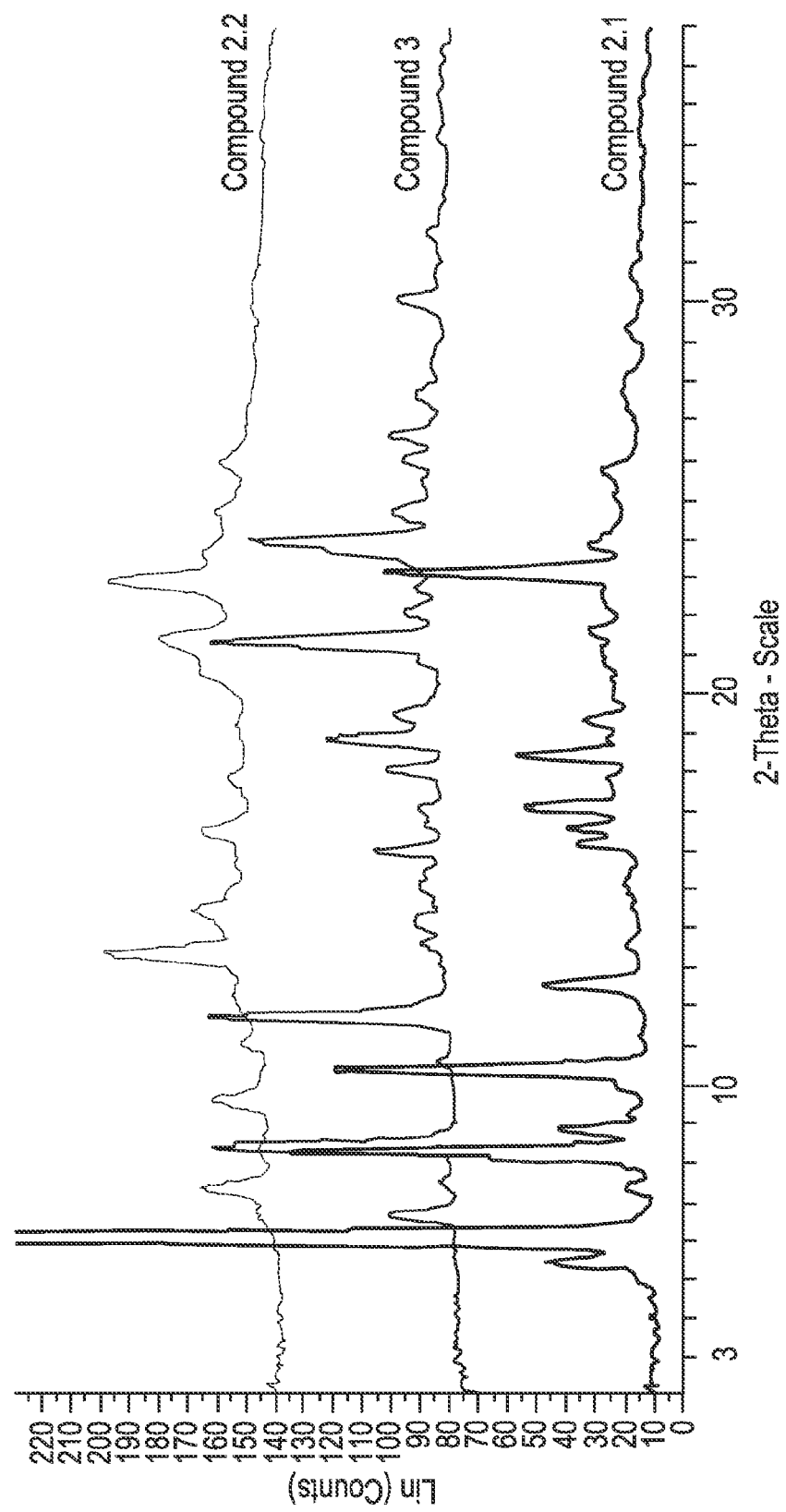
FIG. 9. XRD profiles of Compounds 2.1, 2.2 and 3

As to FIG. 9, powder X-ray diffraction profiles shown therein were obtained by using an X-ray diffractometer equipped with a copper source (Cu/K$_α$ 1.54056 Å). Examples of such diffractometers include the Bruker AXS D8 Discover X-ray Diffractometer and the Rigaku D/Max Rapid X-ray Diffractometer. The Bruker AXS D8 Discover X-ray Diffractometer is equipped with GADDS™ (General Area Diffraction Detection System), a Bruker AXS HI-STAR Area Detector at a distance of 15.05 cm as per system calibration, automated x-y-z stage, and 0.5 mm collimator. The sample is compacted into pellet form and mounted on the x-y-z stage. A diffractogram is acquired (control software: GADDS™ for WNT v4.1.14, © Bruker AXS, 1997-2003) under ambient conditions at a power setting of 40 kV and 40 mA in reflection mode while the sample remains stationary. The exposure time is typically 5 minutes. The diffractogram obtained undergoes a spatial remapping procedure to account for the geometrical pincushion distortion of the area detector, then it is integrated along chi from −118.8 to −61.8° and 2-theta 2.1-37° at a step size of 0.02° with normalization set to bin normalize. In addition to using Jade software, diffraction patterns obtained on the Bruker machine are viewed using EVA software (Analysis software: Diffract$^{Plus}$ EVA, version 9.0, © Bruker AXS, 2003). The Rigaku D/Max Rapid X-ray Diffractometer is equipped with a manual x-y stage, and 0.3 mm collimator. The sample is loaded into a 0.3 mm boron rich glass capillary tube (Charles Supper Company, 15 Tech Circle, Natick, Mass. 01760-1024) by sectioning off one end of the tube and tapping the open, sectioned end into a bed of sample. The loaded capillary is mounted in a holder that was secured into the x-y stage. A diffractogram is acquired under ambient conditions at a power setting of 46 kV at 40 mA in reflection mode, while oscillating about the omega-axis from 0-5° at 1°/sec and spinning about the phi-axis at 2°/sec (Control software: RINT Rapid Control Software, Rigaku Rapid/XRD, version 1.0.0, © Rigaku Co., 1999). The exposure time is typically 5 minutes. The diffractogram obtained is integrated over 2-theta from 2-40 degrees and chi (1 segment) from 0-360° at a step size of 0.02° using the cylint utility in the RINT Rapid display software provided with the instrument (Analysis software: RINT Rapid display software, version 1.18, © Rigaku Co., 1999). The dark counts value is set to 8 as per the system calibration; normalization is set to average; the omega offset is set to 180°; and no chi or phi offsets are used for the integration. Diffraction patterns are viewed using Jade software, which is used to remove the background from the patterns and to assign peak positions (Analysis software: Jade, version 5.0 and 6.0, © Materials Data, Inc., 1995-2004).

Differential Scanning Calorimetry (DSC) experiments were run as follows: An aliquot of a sample was weighed into an aluminum sample pan, (pan part #900793.901; lid part #900794.901; TA Instruments, 109 Lukens Drive, New Castle, Del. 19720), which was sealed by crimping. The sample pan was loaded into the apparatus (Q1000 Differential Scanning Calorimeter, TA Instruments, 109 Lukens Drive, New Castle, Del. 19720). A thermogram was obtained by individually heating the sample at a rate of 10° C./min from T$_{min}$ (typically room temperature) to T$_{max}$ (typically 300° C.) using an empty aluminum hermetic pan as a reference. The control software for both the DSC and TGA experiments was the Advantage for QW-Series, version 1.0.0.78, Thermal Advantage Release 2.0, © TA Instruments—Water LLC, 2001. Dry nitrogen (compressed nitrogen, grade 4.8, BOC Gases, 575 Mountain Avenue, Murray Hill, N.J. 07974-2082) was used as a sample purge gas and was set at a flow rate of 50 mL/min. Thermal transitions were viewed and analyzed using the analysis software provided with the instrument (Analysis Software: Universal Analysis 2000 for Windows 95/95/2000/NT, version 3.1E; Build 3.1.0.40, © TA instruments—Water LLC, 1991-2001).

Thermogravimetric Analysis (TGA) experiements were run as follows: An aliquot of the sample was transferred into a platinum sample pan (pan part #952019.906; TA Instruments, 109 Lukens Drive, New Castle, Del. 19720). The pan was placed on the loading platform and was then automatically loaded into the apparatus (Q500 Thermogravimetric Analyzer, TA Instruments, 109 Lukens Drive, New Castle, Del. 19720) using the control software. Thermograms were obtained by individually heating the sample at 10° C./min from T$_{min}$ (typically room temperature) to T$_{max}$ (typically 300° C.) under flowing dry nitrogen, with a sample purge flow rate of 60 mL/min and a balance purge flow rate of 40 mL/min. Thermal transitions (e.g., weight changes) were viewed and analyzed by using the analysis software provided with the instrument (Analysis Software: Universal Analysis 2000 for Windows 95/95/2000/NT, version 3.1E; Build 3.1.0.40, © TA instruments—Water LLC, 1991-2001).

Chemical names were generated by using ChemDraw (CambridgeSoft, Cambridge, Mass.).

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

Whenever a yield is given as a percentage, such yield refers to a mass of the entity for which the yield is given with respect to the maximum amount of the same entity that could be obtained under the particular stoichiometric conditions. Reagent concentrations that are given as percentages refer to mass ratios, unless indicated differently.

Example 1

[5-(5-Fluoro-4-methyl-1H-benzoimidazol-2-yl)-4-methyl-pyrimidin-2-yl]-[3-(1-methyl-piperidin-4-yl)-propyl]-amine

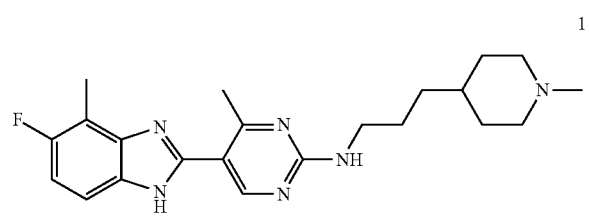 [SMILES: Cc1nc(NCCCC2CCN(C)CC2)ncc1-c1nc2c(C)c(F)ccc2[nH]1]

1

Step A; 4-Methyl-2-ethylsulfanyl-pyrimidine-5-carboxylic acid ethyl ester. A mixture of ethyl acetoacetate (6.37 mL, 50.0 mmol), dimethylformamide dimethylacetal (8.94 g, 75.0 mmol), and catalytic p-toluenesulfonic acid was heated at 100° C. for 2 h. After cooling to rt, the mixture was diluted with 50 mL N,N-dimethylformamide (DMF) and 2-ethyl-isothiourea hydrobromide (9.10 g, 50.0 mmol) was added. After heating the at 100° C. for 18 h, the mixture was cooled to rt and concentrated to give a crude residue, which was purified by FCC (EtOAc/hexanes) to give 7.1 g (61%) of a solid. $^1$H NMR (CDCl$_3$): 8.97-8.91 (m, 1H), 4.43-4.35 (m, 2H), 3.24-3.15 (m, 2H), 2.81-2.72 (m, 3H), 1.47-1.35 (m, 6H).

Step B; 2-Ethanesulfonyl-4-methyl-pyrimidine-5-carboxylic acid ethyl ester. To a 0° C. solution of 4-methyl-2-ethylsulfanyl-pyrimidine-5-carboxylic acid ethyl ester (3 g, 13.3 mmol) in 50 mL dichloromethane (DCM) was added urea hydrogen peroxide (5.20 g, 55.7 mmol) followed by trifluoroacetic anhydride (7.39 mL, 53.1 mmol) dropwise. The solution was warmed to rt for 2 h before quenching with saturated Na$_2$S$_2$O$_{3(aq)}$ (20 mL) and extracting with DCM (100 mL). The organic layer was dried (Na$_2$SO$_4$) and concentrated to give 1.50 g of an orange solid which was used immediately in the next step without purification. $^1$H NMR (CDCl$_3$): 9.28 (s, 1H), 4.47 (q, J=7.2 Hz, 2H), 3.60 (q, J=7.5 Hz, 2H), 2.96 (s, 3H), 1.47-1.42 (m, 6H).

Step C; 4-Methyl-2-[3-(1-methyl-piperidin-4-yl)-propylamino]-pyrimidine-5-carboxylic acid ethyl ester. A mixture of 2-ethanesulfonyl-4-methyl-pyrimidine-5-carboxylic acid ethyl ester (0.30 g, 1.18 mmol) and 3-(1-methyl-piperidin-4-yl)-propylamine (0.18 mg, 1.10 mmol) in EtOH (3 mL) was heated in a sealed tube at 100° C. for 6 h. The mixture was concentrated and purified by FCC to give 200 mg (53%). $^1$H NMR (CDCl$_3$): 8.88-8.72 (m, 1H), 5.60-5.44 (m, 1H), 4.31 (q, J=7.2 Hz, 2H), 3.52-3.39 (m, 2H), 2.91-2.77 (m, 2H), 2.64 (s, 3H), 2.26 (s, 3H), 1.94-1.85 (m, 2H), 1.72-1.57 (m, 4H), 1.41-1.20 (m, 8H).

Step D; {4-Methyl-2-[3-(1-methyl-piperidin-4-yl)-propylamino]-pyrimidin-5-yl}-methanol. To a 0° C. solution of 4-methyl-2-[3-(1-methyl-piperidin-4-yl)-propylamino]-pyrimidine-5-carboxylic acid ethyl ester (0.20 g, 0.63 mmol) in THF (6 mL) was added diisobutylaluminum hydride (1 M in hexanes; 1.25 mL, 1.25 mmol) dropwise. The mixture was warmed to rt over 1 h. The reaction was quenched with 1 M H$_2$SO$_4$ (2 mL). The mixture was neutralized with saturated NaHCO$_{3(aq)}$, and diluted with MeOH (2 mL), CHCl$_3$ (10 mL), and satd. aq. sodium potassium tartrate (10 mL). The mixture was stirred vigourously until the layers separated. The organic layer was dried (Na$_2$SO$_4$) and concentrated to give the crude product (138 mg), which was used in the next step without further purification. $^1$H NMR (CDCl$_3$): 8.07 (s, 1H), 4.52 (s, 2H), 3.42-3.33 (m, 2H), 2.88-2.74 (m, 2H), 2.41 (s, 3H), 2.23 (s, 3H), 1.93-1.83 (m, 2H), 1.72-1.53 (m, 4H), 1.35-1.16 (m, 5H).

Step E; [5-(5-Fluoro-4-methyl-1H-benzoimidazol-2-yl)-pyrimidin-2-yl]-[3-(1-methyl-piperidin-4-yl)-propyl]-amine. To a mixture of 4-methyl-2-[3-(1-methyl-piperidin-4-yl)-propylamino]-pyrimidin-5-yl}-methanol (0.14 g, 0.49 mmol) in toluene (3 mL) was added MnO$_2$ (0.22 g, 2.48 mmol). After 30 min at 70° C., the mixture was filtered through diatomaceous earth. The filtrate was concentrated and immediately dissolved in DMF. A portion of this solution (corresponding to 0.05 g, 0.17 mmol of 4-methyl-2-[3-(1-methyl-piperidin-4-yl)-propylamino]-pyrimidine-5-carbaldehyde) was then treated with 4-fluoro-3-methyl-benzene-1,2-diamine (1.1 equiv.) and Na$_2$H$_2$S$_2$O$_5$ (1.25 equiv.) at 90° C. for 12 h. The reaction mixture was purified by FCC to afford the title compound. MS: mass calcd. for C$_{22}$H$_{29}$FN$_6$, 396.24; m/z found, 397.2 [M+H]$^+$. $^1$H NMR (CD$_3$OD): 8.62 (s, 1H), 7.55 (dd, J=8.0, 3.9 Hz, 1H), 7.17 (dd, J=10.3, 8.8 Hz, 1H), 3.60 (t, J=6.9 Hz, 2H), 3.10-2.99 (m, 2H), 2.71 (s, 3H), 2.66 (d, J=1.4 Hz, 3H), 2.44 (s, 3H), 2.26-2.17 (m, 2H), 1.98-1.88 (m, 2H), 1.87-1.77 (m, 2H), 1.55-1.36 (m, 5H).

In some embodiments Compound 2, shown in Example 2, was synthesized analogously to the procedures described in Example 1.

Example 2

[5-(4,6-Dimethyl-1H-benzoimidazol-2-yl)-4-methyl-pyrimidin-2-yl]-[3-(1-methyl-piperidin-4-yl)-propyl]-amine

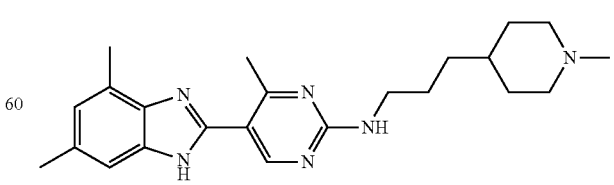

2

MS: mass calcd. for C$_{23}$H$_{32}$N$_6$, 392.27; m/z found, 393.3 [M+H]$^+$. $^1$H NMR (CD$_3$OD): 8.43 (s, 1H), 7.20 (s, 1H), 6.89 (s, 1H), 3.41 (t, J=7.0 Hz, 2H), 2.89-2.82 (m, 2H), 2.54 (s, 3H), 2.53 (s, 3H), 2.42 (s, 3H), 2.25 (s, 3H), 2.05-1.96 (m, 2H), 1.78-1.70 (m, 2H), 1.69-1.59 (m, 2H), 1.34-1.21 (m, 5H).

Example 3

Preparation of 5-(4,6-dimethyl-1H-benzimidazol-2-yl)-4-methyl-N-[3-(1-methyl-4-piperidinyl)-propyl]-2-pyrimidinamine 2,3-dihydroxybutanedioate (1:0.5), polymorph A, Compound 2.1

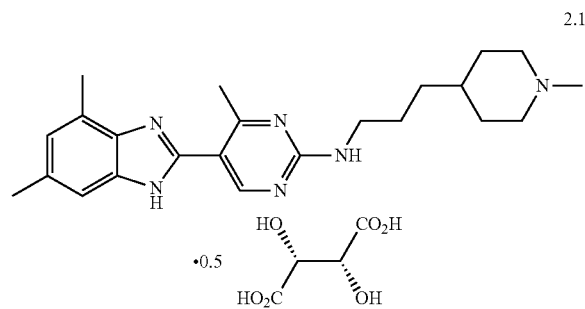

The preparation of 4-methyl-2-((3-(1-methylpiperidin-4-yl)propyl)amino)pyrimidine-5-carbonitrile was described in Schemes 1, 2, 3 and 4 and examples 7, 10, 12, 16, 24 and 25 in U.S. Pat. No. 8,309,720, all of which are incorporated herein by reference.

An alternative procedure for the preparation of 4-methyl-2-((3-(1-methylpiperidin-4-yl)propyl)amino)pyrimidine-5-carbonitrile used in the preparation of Compound 2.1 is as follows. To a solution of 4-methyl-2-(methylsulfonyl)pyrimidine-5-carbonitrile (21.64 g, 109.7 mmol) in toluene (260 g) was added 3-(1-methylpiperidin-4-yl)propan-1-amine (14.30 g, 91.5 mmol) in 10% $K_2CO_{3(aq)}$ (110.2 g, 100 mL). The reaction was heated to 60-65° C. for 20 minutes. The aqueous layer was then removed and to the organic layer was added 1M NaOH (110.1 g). The mixture was reheated to 65° C., stirred for 10 minutes and the aqueous layer was removed. To the organic layer, water (110.8 g) was added and the solution reheated to 65° C. for 10 minutes. The aqueous layer was removed and the organic layer was concentrated under reduced pressure. 4-methyl-2-((3-(1-methylpiperidin-4-yl)propyl)amino)pyrimidine-5-carbonitrile was then crystallized from a solution of toluene (approximately 65 g) at a temperature of about 65° C. to provide 21.20 g of 4-methyl-2-((3-(1-methylpiperidin-4-yl)propyl)amino)pyrimidine-5-carbonitrile.

Step A

A 100 L glass-lined reactor was charged with 4-methyl-2-((3-(1-methylpiperidin-4-yl)propyl)amino)pyrimidine-5-carbonitrile (5.41 kg, 19.8 mol) and toluene (47.13 kg). The resultant suspension was stirred and cooled to about 0 to −5° C. Next, 1.0 M diisobutylaluminum hydride (DIBAL-H) in toluene (40.55 kg, 47.33 mol) was added, via nitrogen pressure, while maintaining the internal reaction temperature at <2° C. After completing the addition, the resultant reaction solution was warmed to about 5-10° C. and the reaction monitored for completion by HPLC. Cold ethyl acetate (4.89 kg) was then added over 30 min and the resultant mixture stirred for 15-20 minutes. The resultant mixture (containing 4-methyl-2-((3-(1-methylpiperidin-4-yl)propyl)amino)pyrimidine-5-carbaldehyde) was transferred to a 100 L glass receiver and rinsed with toluene (1.00 kg).

An alternative procedure to prepare 4-methyl-2-((3-(1-methylpiperidin-4-yl)propyl)amino)pyrimidine-5-carbaldehyde is as follows. 4-methyl-2-((3-(1-methylpiperidin-4-yl)propyl)amino)pyrimidine-5-carbonitrile ("compound 1-E-2") was dissolved in acetic acid (1.32 kg per kg of compound 1-E-2). A catalyst which is a fine grained solid composed mostly of nickel derived from a nickel-aluminum alloy, such as Raney nickel, type 3202, (55% w/w suspension in water, 0.29 g per g of compound 1-E-2) was added and the reaction was placed under an atmosphere of $H_2$,(p($H_2$)=1-1.3 bar) at T=25° C. When the reaction was complete as judged by there being not more than about 3% of compound 1-E-2 remaining, the reaction mixture was filtered and the filtrate neutralized to pH=7 with aqueous potassium carbonate (50% w/w) solution. Succinic anhydride (0.185 g per g of initial amount of compound 1-E-2) was added. Toluene (4.5 g per g of initial amount of compound 1-E-2) was added and additional aqueous potassium carbonate 50% was added to adjust the pH of the solution to pH>9, in some embodiments to pH=9.5. The layers in such bi-phasic organic-aqueous medium were separated and the aqueous layer was washed once with toluene (0.5 g per g of initial amount of compound 1-E-2). The united organic layers were then extracted with an aqueous solution at a pH of equal to or less than about 4, in some embodiments at pH of about 3.5. In some embodiments, such solution was an 8% aqueous HCl solution (1.01 g per g of initial amount of compound 1-E-2). This aqueous phase, containing 4-methyl-2-((3-(1-methylpiperidin-4-yl)propyl)amino)pyrimidine-5-carbaldehyde, was used without further work-up in the next step A-1. The so-prepared carbaldehyde solution could be used in further steps to prepare compounds according to this invention, such as compounds 2, 2.1 and 3.

Step A-1

In some embodiments, in a separate vessel sodium sulfite (1.2 equivalents (eq) relative to the initial amount of compound 1-E-2), 1,2-diamino-3,5-dimethylbenzene dihydrochloride (1.2 equivalents (eq) relative to the initial amount of compound 1-E-2) and water (5.74 g per g of the initial amount of compound 1-E-2) were stirred at room temperature. Hydrochloric acid (37%, 0.24 g per g of the initial amount of compound 1-E-2) was added and the reaction was heated to 50° C. within 20 minutes and air flow was circulated through the solution. Compound B33 in aqueous solution, prepared for example as indicated above, was added to this reaction mixture over 1.5 h. The reaction was heated to a temperature of about 55-60° C. for approximately 1-2.5 h. In a subsequent step, the solids were filtered off and 2-methyltetrahydrofuran (7.18 g per g of the initial amount of compound 1-E-2) was added to the filtrate. In a subsequent step, 30% $NaOH_{(aq)}$ (1.1-1.2 g per g of the initial amount of compound 1-E-2) was added to adjust the pH to approximately 9.5-11.5. The reaction mixture was heated to 45-50° C. for 15 min. The aqueous layer was removed, and water (0.65 g per g of the initial amount of compound 1-E-2) and 30% $NaOH_{(aq)}$ (0.18 g per g of the initial amount of compound 1-E-2) was added to the organic layer, which was heated to 45-50° C. for 5-15 min. The aqueous layer in the resulting bi-phasic medium was removed and discarded, and water (0.62 g per g of the initial amount of compound 1-E-2) was added to the organic layer thus forming another bi-phasic medium, which was heated to 45-50° C. for 5-15 min. The aqueous layer from such bi-phasic medium was removed and discarded, cyclohexane added to the organic layer, which was heated to 45-50° C., and solid Compound 2 was obtained by cooling it to 0-5° C., crystallizing Compound 2 out of it, and isolating it by filtration.

Step B

A cold solution of water/sulfuric acid (27.05 kg/2.26 kg) was added to each, a 100 L Hastelloy reactor and a 100 L glass lined reactor. The resultant aqueous acid solutions were stirred and cooled to about 2-5° C. Maintaining the temperature <30° C. at all times, 50% (by volume) of the mixture prepared in STEP A above was added to each aqueous sulfuric acid solution. The resultant suspension was checked for pH (target pH of 4-5) and stirred at about 20-25° C. for about 1.5-2 h. The suspensions were then cooled to about 10-15° C. and the pH of the suspensions adjusted to pH~1-12, by adding 6N sodium hydroxide (16.12 kg, 81.42 mol), over 20 min. The resultant mixtures were then stirred for an additional 15-20 minutes, the agitation was then stopped and the phases allowed to separate.

The organic phases were removed from the top of each reactor via vacuum and combined. Then the aqueous phase and middle oil phases were drained via the bottom valve of each reactor and discarded. The combined organic phase was concentrated at ~40° C. to yield a solid. This solid was transferred to drying trays and dried (60 Torr, 30-35° C.) overnight to yield solid 4-methyl-2-((3-(1-methylpiperidin-4-yl)propyl)amino)pyrimidine-5-carbaldehyde.

Step C

In a 100 L glass-lined reactor, sodium metabisulfite ($Na_2S_2O_5$) (1.96 kg, 9.79 mol) was dissolved in purified water (54.63 kg), followed by the addition of 3,5-dimethyl-1,2-benzenediamine-2HCl (2.07 kg, 9.86 mol) and the resultant mixture stirred at about 20-25° C. to effect solution. Next, concentrated hydrochloric acid (1.65 kg, 16.79 mol) was added, followed by addition of 4-methyl-2-((3-(1-methylpiperidin-4-yl)propyl)amino)pyrimidine-5-carbaldehyde, prepared as in STEP B above (2.74 kg, 9.79 mol) and the resultant mixture stirred at about 23-27° C. to effect solution. The resultant mixture was heated to about 57-62° C. and monitored for completion by HPLC. The reaction mixture was cooled to about 20-25° C. and then half of the volume (~30 L) was then added, via a metering pump, to a stirring 50 L glass reactor system containing a solution of potassium carbonate (3.9 kg, 28.2 mol) dissolved in purified water (15 kg), resulting in the formation of a precipitate. The precipitated product was stirred for ~1 h and then allowed to settle. The clear supernatant (~20 L) was removed from the top of the 50 L reactor system and purified water (~20 kg) was added. The resultant mixture was stirred for 10 min, filtered, washed with water (13 kg) and dried at 35-40° C. under vacuum to yield solid [5-(4,6-dimethyl-1H-benzoimidazol-2-yl)-4-methyl-pyrimidin-2-yl]-[3-(1-methyl-piperidin-4-yl)-propyl]-amine, compound 2. MS: $[M+H]^2$=393, $^1H$ NMR (600 MHz, Methanol-$d_6$) δ, 1.38-1.43 (m, 2H), 1.43-1.52 (m, 2H), 1.53-1.61 (br m, 1H), 1.64-1.71 (m, 2H), 1.90-1.96 (br m, 2H), 2.42 (s, 3H), 2.53 (s, 3H), 2.54 (s, 3H), 2.74 (s, 3H), 2.78-2.86 (br m, 2H), 3.15-3.36 (m, 2H), 3.36-3.47 (m, 2H) 4.35 (s, 1H), 6.90 (s, 1H), 7.20 (s, 1H), 8.44 (br s, 1H).

Step D: Preparation of Hemi-Tartrate of [5-(4,6-dimethyl-1H-benzoimidazol-2-yl)-4-methyl-pyrimidin-2-yl]-[3-(1-methyl-piperidin-4-yl)-propyl]-amine In a 100 L Hastelloy reactor, [5-(4,6-dimethyl-1H-benzoimidazol-2-yl)-4-methyl-pyrimidin-2-yl]-[3-(1-methyl-piperidin-4-yl)-propyl]-amine, prepared as indicated above (6.58 kg, 15.56 mol) was dissolved in a medium containing at least one low-alkyl alcohol, which in an embodiment was denatured ethanol (31.00 kg), at about 48-52° C., denatured ethanol being 95:5 (volume ratio) ethanol:2-propanol mixture.

After stirring for 15 minutes, the resultant hazy solution was cooled to about 25-30° C. Magnesium sulfate (0.60 kg) was added and the resultant mixture was stirred an additional 30 minutes. The magnesium sulfate was filtered over CELITE® (0.30 kg) and the resultant clear solution (Karl Fischer titration, measured water content=0.22%) was transferred to a clean 100 L glass-lined reactor and heated to about 48-52° C. A solution of L-(+)-tartaric acid (1.16 kg, 7.73 mol) in a medium containing at least one low-alkyl alcohol, which in an embodiment was denatured ethanol (10.0 kg) was charged to the reactor over 20 minutes. The resultant hemi-tartrate salt alcohol mixture was heated to about 70-75° C. and then aged for 1 h. The resultant yellow slurry was cooled to about 0-5° C. over a 2 h period and then aged for 20 min. The product (as a precipitate) was filtered, washed with cold denatured ethanol (5.20 kg), then dried at about 75-80° C. under vacuum to yield the [5-(4,6-dimethyl-1H-benzoimidazol-2-yl)-4-methyl-pyrimidin-2-yl]-[3-(1-methyl-piperidin-4-yl)-propyl]-amine, as its corresponding hemi-tartrate solid salt, compound 2.1. Because more than one crystallization is performed according to this invention, the crystallization referred to above for Compound 2.1 is sometimes refered to as a first crystallization. When accompanying the term crystallization throughout this specification, ordinal terms are used for reference purposes, and the use of a certain ordinal term does not necessarily imply that the corresponding operations characterized by preceding ordinal terms must necessarily be peformed too.

Step E: Recrystallization

Method E-S. In a 100 L Hastelloy reactor, the hemi-tartrate of [5-(4,6-dimethyl-1H-benzoimidazol-2-yl)-4-methyl-pyrimidin-2-yl]-[3-(1-methyl-piperidin-4-yl)-propyl]-amine, compound 2.1, prepared as in STEP D above (5.19 kg, 11.10 mol) was dissolved in a low-alkyl alcohol-containing medium, which in an embodiment was a hydroalcoholic solvent, which in an embodiment was a mixture of denatured ethanol (32.40 kg) and water (2.62 kg) at about 75-78° C. The resultant solution was cooled to about 50-55° C. and polish filtered (to remove any foreign particles) into a clean 100 L glass-lined reactor, followed by a rinse with denatured ethanol (4.15 kg). A solvent containing at least one low-alkyl alcohol, which in an embodiment was denatured ethanol (25.62 kg) was added and the resultant solution was stirred and heated to about 78-80° C. to atmospherically distill off 51 L of the solvent. The resultant solution was cooled to about 55-60° C. and additional solvent containing at least one low-alkyl alcohol, which in an embodiment was denatured ethanol (27.63 kg) was added, followed by heating to about 78-80° C. to atmospherically distill off 27 L of the solvent. The resultant solution was then cooled to about 50-55° C., seeded with Compound 2.1 seeds (2.0 g, 4.3 mmol), then further cooled to about 18-22° C. and then stirred for 1 h. The resultant precipitate was filtered, washed with denatured ethanol (5.00 kg) and dried at about 75-80° C. under vacuum to yield the solid hemi-tartrate of [5-(4,6-dimethyl-1H-benzoimidazol-2-yl)-4-methyl-pyrimidin-2-yl]-[3-(1-methyl-piperidin-4-yl)-propyl]-amine (compound 2.1); melting point 179° C.

Figure 6:
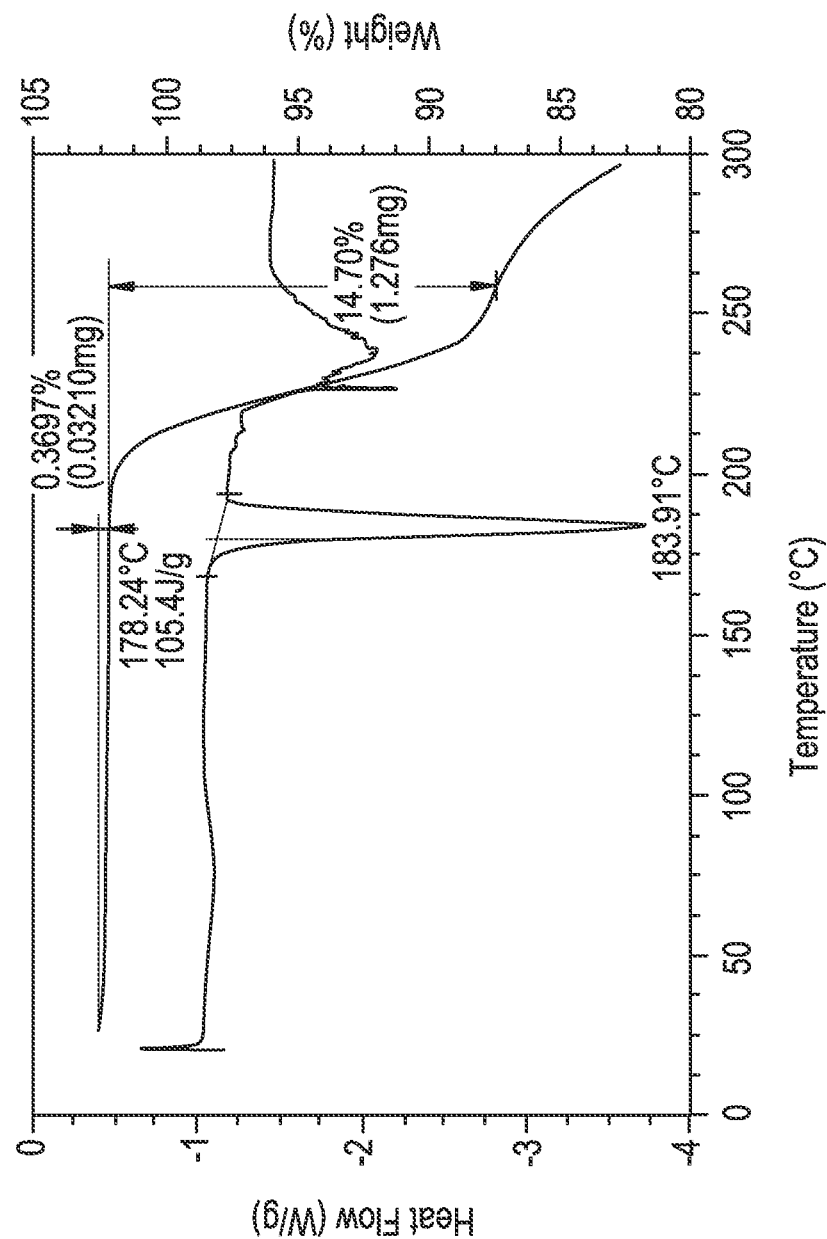
FIG. 6. Differential Scanning Calorimetry (DSC) and Thermogravimetric Analysis (TGA) of Compound 2.1

Method E-T. An alternative procedure for the recrystallization of compound 2.1; hemi-tartrate of [5-(4,6-Dimethyl- 1H-benzoimidazol-2-yl)-4-methyl-pyrimidin-2-yl]-[3-(1-methyl-piperidin-4-yl)-propyl]-amine: A 500 mL-reactor was charged with [5-(4,6-dimethyl-1H-benzoimidazol-2-yl)-4-methyl-pyrimidin-2-yl]-[3-(1-methyl-piperidin-4-yl)-propyl]-amine hemi-tartrate (24.0 g, 25.7 mmol) and a low-alkyl alcohol-containing medium, which in an embodiment was a medium containing at least one a low-alkyl alcohol, which in an embodiment was an alcohol, which in an embodiment was methanol (63.0 g). The resulting mixture was warmed to 50° C. for 15 min, until all the solids were observed to dissolve. A low-alkyl alcohol-containing medium, which in an embodiment was a medium containing at least one a low-alkyl alcohol, which in an embodiment was denatured ethanol (105.0 g) was then added and the resulting solution was filtered (at 50° C.) to remove any remaining particles. The filtrate was heated briefly to reflux, then cooled to approx. 60° C., before seeding with crystals of Compound 2.1. The resulting mixture was subjected to the following temperature profile for crystallization: 1 h at 60° C., cooling to 40° C. over 2 h, heating to 50° C. over 1 h, cooling to 30° C. over 2 h, heating to 40° C. over 1 h, cooling to 20° C. over 2 h, heating to 30° C. over 1 h, cooling to 10° C. over 2 h, heating to 20° C. over 1 h, then cooling to 0° C. over 2 h. The resulting suspension was maintained at 0° C. for 7 h, then the resulting solid precipitate was isolated by suction filtration, washed with denatured ethanol (3×30.0 g) and dried in vacuo at 40° C. to yield Compound, 2.1 as a white crystalline solid. FIG. 6 shows the differential scanning calorimetry (DSC) and thermo gravimetric analysis (TGA) profiles of Compound 2.1.

Because more than one crystallization is performed according to this invention, the recrystallization referred to above for Compound 2.1 is sometimes refered to as a second crystallization. Whether recrystallized according to method E-S or E-T, the $^1$H NMR of a sample of the anhydrous hemi-tartrate of [5-(4,6-dimethyl-1H-benzoimidazol-2-yl)-4-methyl-pyrimidin-2-yl]-[3-(1-methyl-piperidin-4-yl)-propyl]-amine, compound 2.1: $^1$H NMR (300 MHz, Methanol-$d_4$) δ, 8.44 (br, s, 1H), 7.20 (s, 1H), 6.90 (s, 1H), 4.35 (s, 1H), 3.35-3.48 (m, 4H), 2.76-2.89 (o, m, 2H), 2.75 (s, 3H), 2.54 (s, 3H), 2.53 (s, 3H), 2.42 (s, 3H), 1.88-1.99 (br, m, 2H), 1.34-1.75 (m, o, 7H).

Compound 2.1 has an aqueous solubility at room temperature of about 1.1 g/ml. This compound is hygroscopic. It converts to Compound 3 at above 70% relative humidity, and it forms the tetrahydrate Compound 3 in aqueous solution.

Embodiments of Compound 2.1 obtained as described in this Example 3 had purity equal to or about 98.95% Recrystallization produced embodiments of the same compound with purity equal to or about 99.23%. Purity changes upon recrystallization of Compound 2.1 are shown in Table 1. Impurities I1-I11 and A1-A19 referred to in various of the Tables presented herein are characterized in Table 9 and its associated chemical structures in Example 11, and also in Tables 1 and 7.

TABLE 1

| Impurity | m/z [M + H]⁺ | Relative retention time (RRT) | Average impurities (%) of Compound 2.1 before recrystallization | Average impurities (%) of Compound 2.1 after recrystallization |
| --- | --- | --- | --- | --- |
| I1 or A1 | 278 | 0.32 | na | nd |
| A2 | 276 | 0.48 | 0.01 | nd |
| I3 or A3 | 277 | 0.73 | nd | nd |
| A4 | 395 | 0.81 | 0.03 | nd |

TABLE 1-continued

| Impurity | m/z [M + H]⁺ | Relative retention time (RRT) | Average impurities (%) of Compound 2.1 before recrystallization | Average impurities (%) of Compound 2.1 after recrystallization |
| --- | --- | --- | --- | --- |
| I5 or A5 | 653 | 0.86 | 0.24 | 0.154 |
| A6 | unk | 0.87 | nd | 0.01 |
| A7 | 274/733 | 0.89 | 0.09 | 0.06 |
| A8a & A8b | 653/unk | 0.91 | 0.11 | 0.02 |
| I8 or A9 | 505 | 0.93 | 0.02 | 0.02 |
| A10 | unk | 0.95 | 0.03 | 0.01 |
| A11 | unk | 0.97 | 0.02 | 0.01 |
| A12 | unk | 0.98 | 0.02 | 0.02 |
| Compound 2.1 | 393 | 1.00 | 98.95 | 99.23 |
| A13 | unk | 1.03 | nd | 0.01 |
| I7 or A14 | 407 | 1.04 | 0.18 | 0.23 |
| A15 | unk | 1.048 | nd | Nd |
| A16 | unk | 1.057 | nd | 0.01 |
| A17 | unk | 1.064 | 0.01 | 0.03 |
| A18a & A18b | 512/409 | 1.07 | 0.08 | 0.04 |
| A19 | unk | 1.08 | 0.03 | 0.01 |
| A20 | unk | 1.10 | 0.06 | 0.04 |
| A21 | unk | 1.14 | 0.04 | Nd |
| A22 | 847 | 1.17 | 0.05 | 0.02 |

Abbreviations used in the immediately preceding Table:
nd = not detected,
unk = unknown,
na = not analyzed As displayed in FIG. 6, the anhydrous form 2.1 shows an initial 0.3% weight loss up to 170° C. of the surface moisture, and subsequently the appropriate stoichiometric (0.5 mol) weight loss of tartaric acid (~15%, 16.05% theoretical). The melting point is a fairly sharp endotherm with a peak max at 184° C.

Example 4

Examples 4-1 and 4-2

Preparation of 5-(4,6-dimethyl-1H-benzimidazol-2-yl)-4-methyl-N-[3-(1-methyl-4-piperidinyl)-propyl]-2-pyrimidinamine 2,3-dihydroxybutanedioate (1:0.5), polymorph B, Compound 2.2, from Compound 2.1.

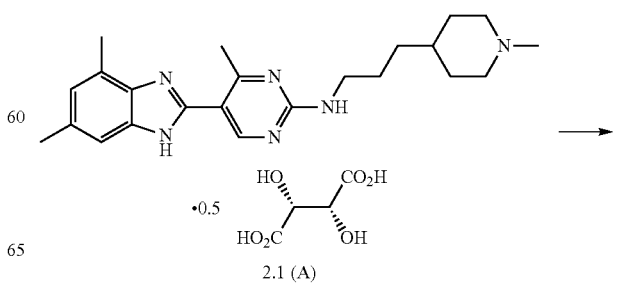

2.1 (A)

-continued

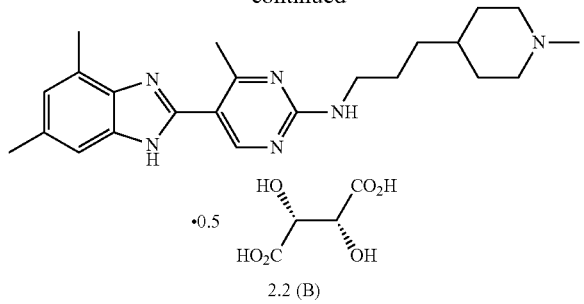

2.2 (B)

Example 4-1

In a 10 mL glass tube equipped with a magnetic stirring bar, 5-(4,6-dimethyl-1H-benzimidazol-2-yl)-4-methyl-N-[3-(1-methyl-4-piperidinyl)propyl]-2-pyrimidinamine 2,3-dihydroxybutanedioate (1:0.5), compound 2.1 (1 g) was dissolved in water (10 mL) at room temperature (22° C.). The clear yellowish solution was stirred at room temperature overnight, then cooled to 2.5° C. for 2 hours, before the product was isolated by filtration and dried in vacuo overnight at 55° C. to yield 0.9 g of compound 2.2 (water content 4.9%).

Example 4-2

In other embodiments, Compound 2.2 was prepared as follows. In a 10 mL glass tube equipped with a magnetic stirring bar, 5-(4,6-dimethyl-1H-benzimidazol-2-yl)-4-methyl-N-[3-(1-methyl-4-piperidinyl)propyl]-2-pyrimidinamine 2,3-dihydroxybutanedioate (1:0.5), compound 2.1 (0.5 g) was dissolved in a mixture of water (4.5 mL) and 2-propanol (0.5 mL) at 50° C. The clear yellowish solution was cooled to 10° C. within 2 hours leading to crystallization of a white solid. The resulting thick suspension is kept at 10° C. overnight, the product is then isolated by filtration and dried in vacuo for 21 h to yield 0.43 g of compound 2.2.

Figure 8:
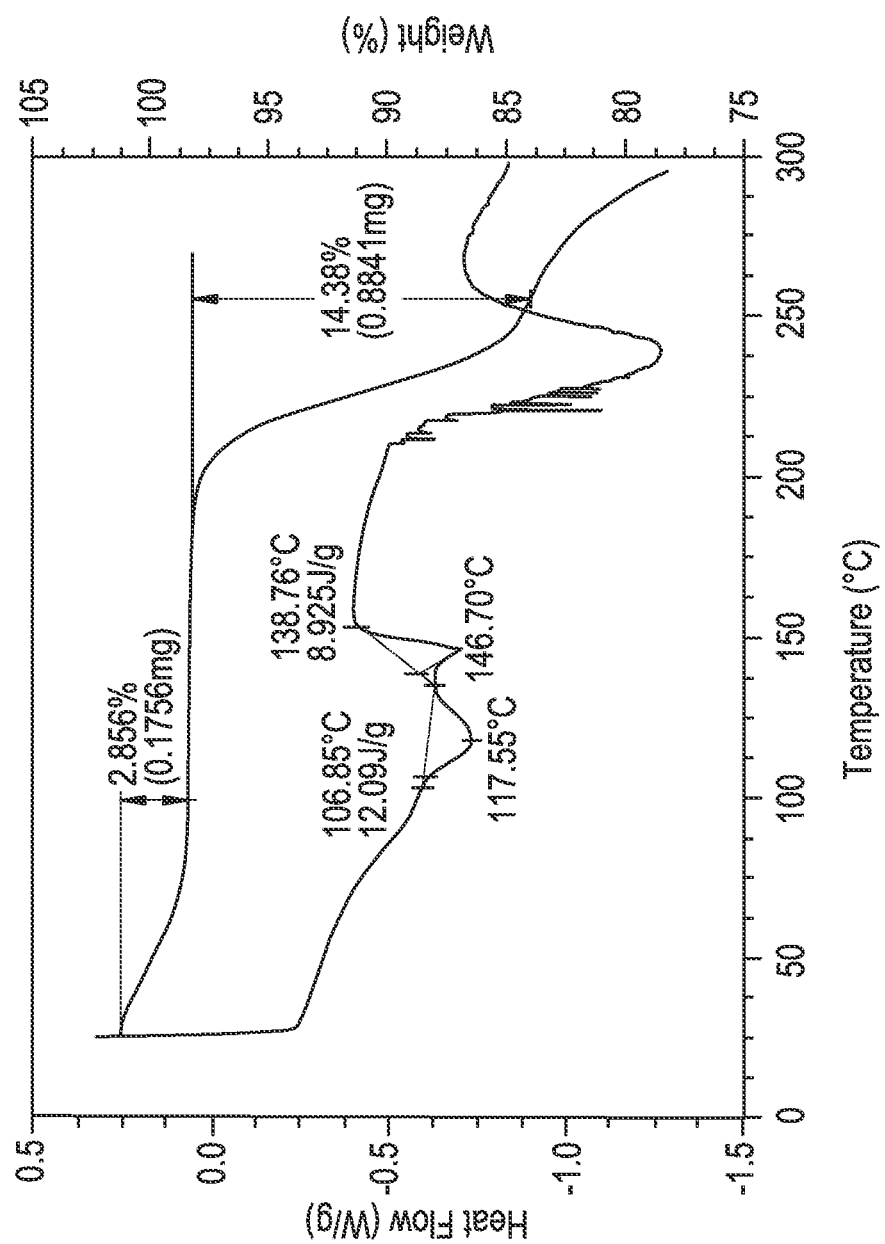
FIG. 8. DSC and TGA of Compound 2.2

The powder X-ray diffraction (XRD) pattern of an embodiment of compound 2.2, Example 4.2, is shown in FIG. 1, and the XRD peak lists are shown in Tables 2 and 2.1. FIG. 8 shows the differential scanning calorimetry (DCS) and thermo gravimetric analysis (TGA) profiles of Compound 2.2.

TABLE 2

XRD Peak list for an embodiment of Compound 2.2 with relative intensity of at least 9%

| Position [°2θ] | d-spacing [Å] | Intensity (counts) | Relative Intensity (%) |
|---|---|---|---|
| 6.96 | 12.69 | 186 | 11.1 |
| 7.67 | 11.52 | 586 | 34.8 |
| 8.26 | 10.70 | 291 | 17.3 |
| 8.63 | 10.24 | 256 | 15.2 |
| 9.91 | 8.92 | 413 | 24.6 |
| 11.34 | 7.80 | 153 | 9.1 |
| 12.09 | 7.31 | 344 | 20.5 |
| 13.66 | 6.48 | 1682 | 100.0 |
| 14.73 | 6.01 | 579 | 34.4 |
| 16.85 | 5.26 | 677 | 40.2 |
| 18.21 | 4.87 | 385 | 22.9 |
| 19.24 | 4.61 | 279 | 16.6 |
| 20.89 | 4.25 | 417 | 24.8 |
| 23.25 | 3.82 | 1378 | 81.9 |
| 23.98 | 3.71 | 611 | 36.3 |

TABLE 2-continued

XRD Peak list for an embodiment of Compound 2.2 with relative intensity of at least 9%

| Position [°2θ] | d-spacing [Å] | Intensity (counts) | Relative Intensity (%) |
|---|---|---|---|
| 25.04 | 3.55 | 296 | 17.6 |
| 26.25 | 3.39 | 318 | 18.9 |

TABLE 2.1

XRD Peak list for an embodiment of Compound 2.2 with relative intensity of at least 20%

| Position [°2θ] | d-spacing [Å] | Intensity (counts) | Relative Intensity (%) |
|---|---|---|---|
| 7.67 | 11.52 | 586 | 34.8 |
| 9.91 | 8.92 | 413 | 24.6 |
| 12.09 | 7.31 | 344 | 20.5 |
| 13.66 | 6.48 | 1682 | 100.0 |
| 14.73 | 6.01 | 579 | 34.4 |
| 16.85 | 5.26 | 677 | 40.2 |
| 18.21 | 4.87 | 385 | 22.9 |
| 20.89 | 4.25 | 417 | 24.8 |
| 23.25 | 3.82 | 1378 | 81.9 |
| 23.98 | 3.71 | 611 | 36.3 |

Compound 2.2 is physically stable only when stored in a tightly sealed vial at ambient condition. It absorbs water readily and converts to Compound 3 when exposed to the atmosphere.

When purification by recrystallization of Compound 2.1 was attempted by using alternative conditions, such as by using water:2-propanol (90:10, weight ratio) and overnight in-vacuo drying at 55° C., compound 2.1 was expected, but instead compound 2.2 was obtained. In another alternative recrystallization process using water and then isolation by filtration and in-vacuo drying for 21 h, Compound 2.2 was also obtained instead of the expected Compound 2.1. In contrast, recrystallization of Compound 3 does not present this polymorphism generation, but it generates one singly characterized form of the same Compound.

Example 5

Preparation of 5-(4,6-dimethyl-1H-benzimidazol-2-yl)-4-methyl-N-[3-(1-methyl-4-piperidinyl)-propyl]-2-pyrimidinamine 2,3-dihydroxybutanedioate tetrahydrate (1:0.5:4), Compound 3, from the free base Compound 2

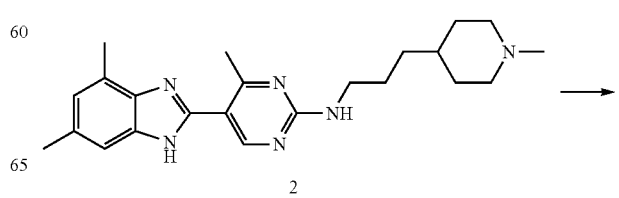

2

-continued

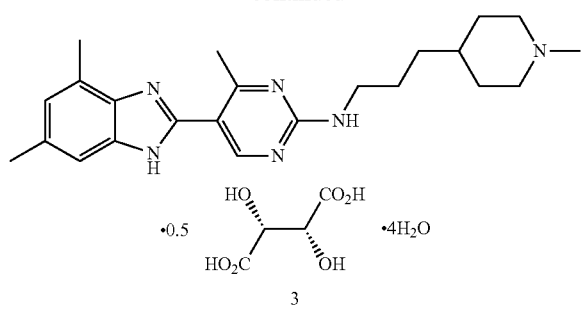

3

Figure 2:
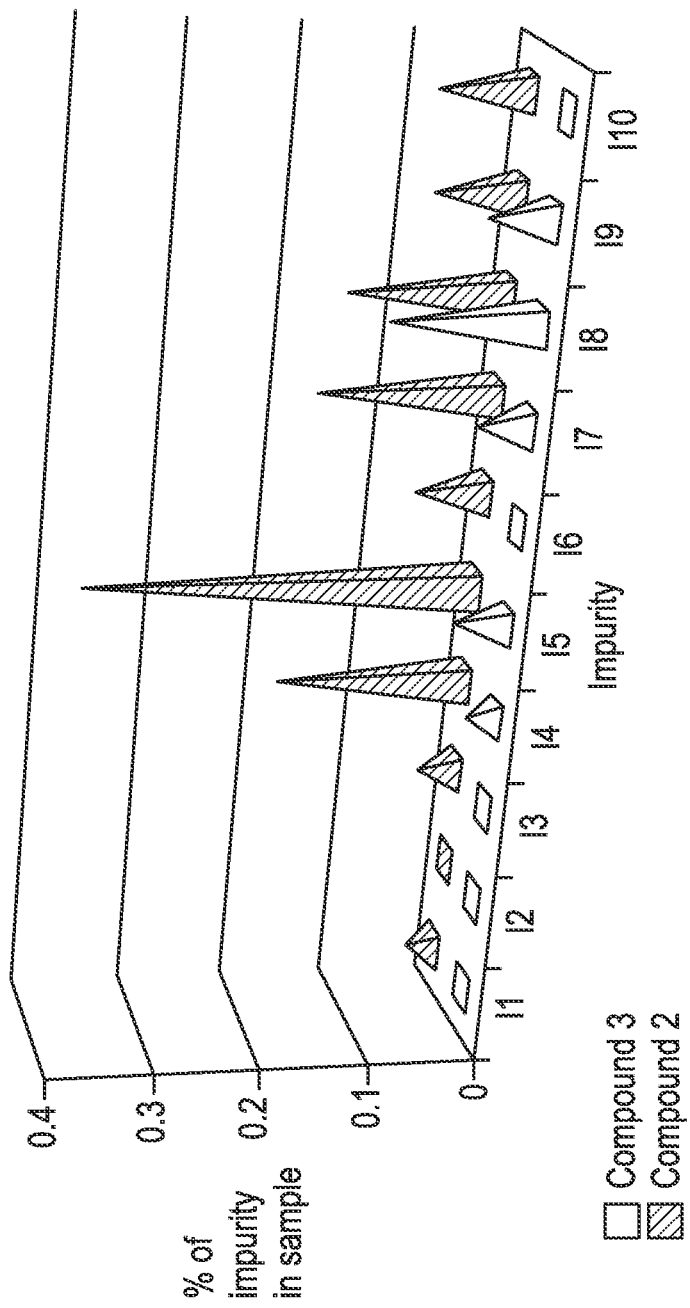
FIG. 2. Comparison of impurity segregation profiles for Compounds 2 and 3 (See also Example 5)

A glass reactor with mechanical stirrer was charged with 5-(4,6-dimethyl-1H-benzimidazol-2-yl)-4-methyl-N-[3-(1-methyl-4-piperidinyl)propyl]-2-pyrimidinamine), compound 2 (10.0 g, 25.2 mmol (assay-corrected as appropriate to this equivalent amount depending on purity)), L-(+)-tartaric acid (1.90 g, 12.5 mmol) and water (75.1 g) at 20° C. The reaction mixture was heated to reflux until the solid was completely dissolved. The clear solution was then cooled to 35° C. and seeding crystals of 5-(4,6-dimethyl-1H-benzimidazol-2-yl)-4-methyl-N-[3-(1-methyl-4-piperidinyl)-propyl]-2-pyrimidinamine 2,3-dihydroxybutanedioate tetrahydrate (1:0.5:4), compound 3.S (prepared in Example 6) were added. After gradually cooling to 5° C. overnight, the product was isolated by suction filtration and the filter cake washed with water (10 g). The solid was dried in vacuo (at ca. 200 mbar) with a gas bleed to yield the title Compound 3 (93.2% yield). Table 3 and FIG. 2 display the impurity profiles for Compounds 2 and 3, according to this example, showing that the impurity profile of Compound 3 is significantly reduced with respect to that of Compound 2.

TABLE 3

Impurity Profile for Compounds 2 and 3, (Example 5)

|  | Compound 2 | Compound 3 |
| --- | --- | --- |
| Impurity 1 (I1) | 0.03 | 0 |
| Impurity 2 (I2) | 0 | 0 |
| Impurity 3 (I3) | 0.04 | 0 |
| Impurity 4 (I4) | 0.18 | 0.03 |
| Impurity 5 (I5) | 0.37 | 0.05 |
| Impurity 6 (I6) | 0.07 | 0 |
| Impurity 7 (I7) | 0.17 | 0.05 |
| Impurity 8 (I8) | 0.15 | 0.14 |
| Impurity 9 (I9) | 0.08 | 0.06 |
| Impurity 10 (I10) | 0.09 | 0 |

Figure 7:
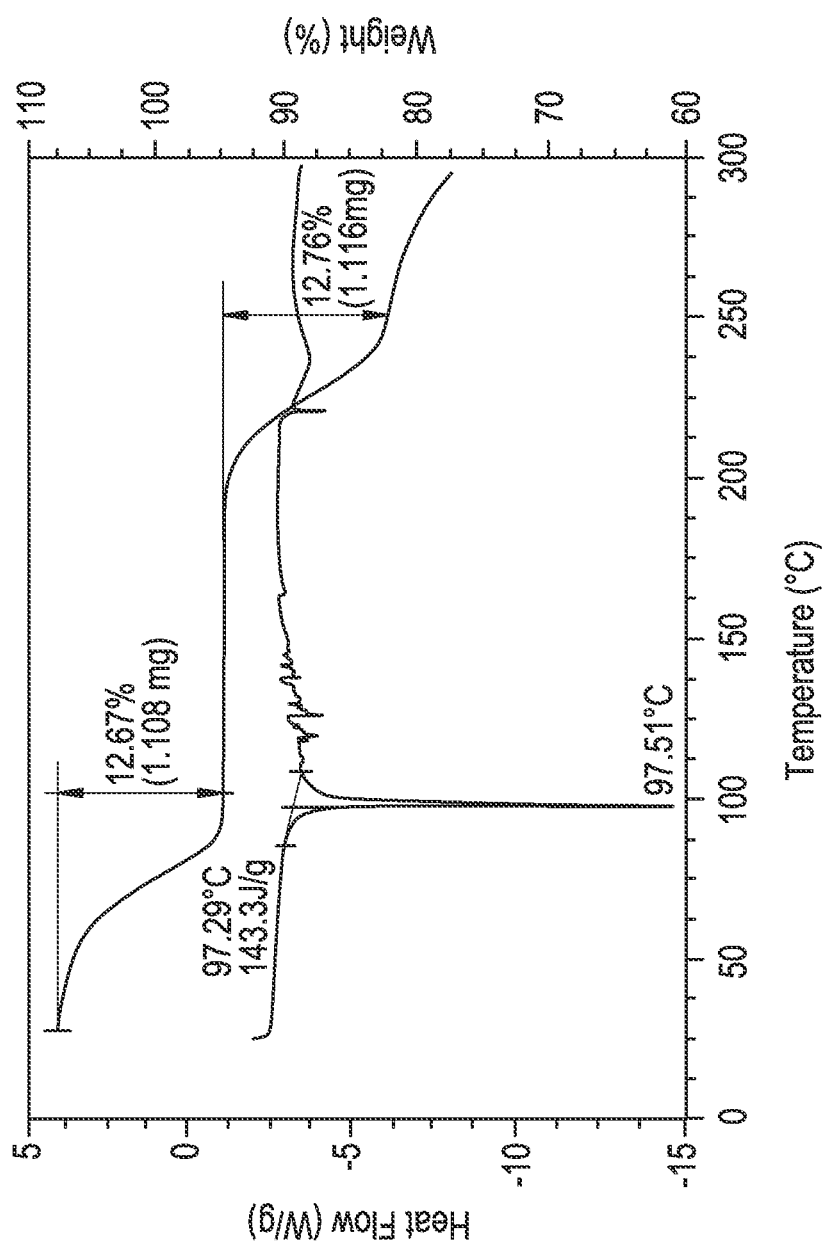
FIG. 7. DSC and TGA of Compound 3

The DSC and TGA profiles of Compound 3 (FIG. 7) show an initial 12.7% water loss before 100° C., corresponding to ~4 mol of water (13.3% calculated) followed by a 12.8% weight loss of the tartaric acid. The melting point is a sharp endotherm with a peak max at 97.5° C., and the endotherm at 184° C., which is characteristic of the anhydrous form, is no longer present.

Example 6

Preparation of Seeding Crystals-5-(4,6-dimethyl-1H-benzimidazol-2-yl)-4-methyl-N-[3-(1-methyl-4-piperidinyl)-propyl]-2-pyrimidinamine 2,3-dihydroxybutanedioate hydrate (1:0.5:4), Compound 3.S, that was used, for example, in the seeding described in Example 7

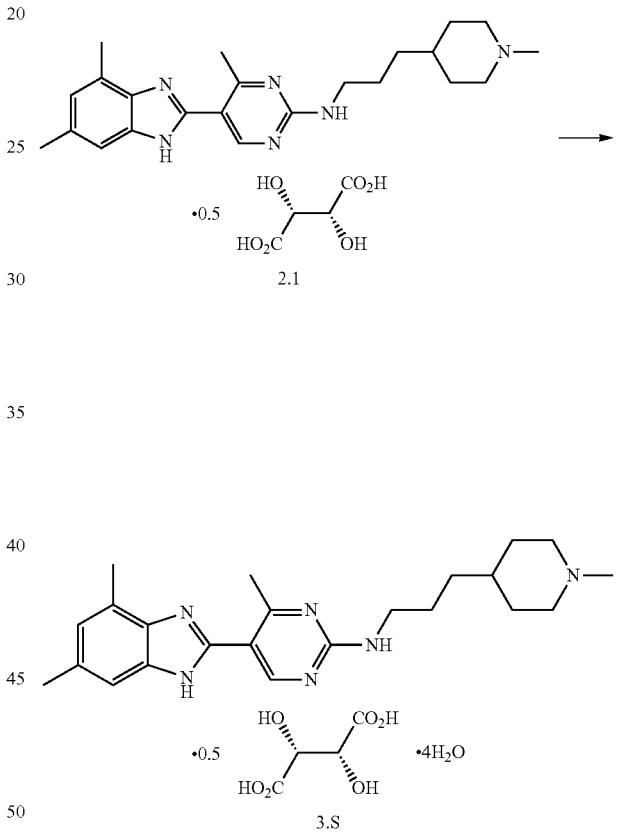

In a glass tube with magnetic stirring bar, (5-(4,6-dimethyl-1H-benzimidazol-2-yl)-4-methyl-N-[3-(1-methyl-4-piperidinyl)propyl]-2-pyrimidinamine 2,3-dihydroxybutanedioate (1:0.5)), compound 2.1 (crude) was dissolved in water at 60° C. The solution was cooled to room temperature, then stirred overnight. A yellowish suspension formed. After cooling the reaction mixture to 2.5° C. for 1.5 h, the solid was isolated by filtration and washed with water to provide 5-(4,6-dimethyl-1H-benzimidazol-2-yl)-4-methyl-N-[3-(1-methyl-4-piperidinyl)-propyl]-2-pyrimidinamine 2,3-dihydroxybutanedioate hydrate (1:0.5:4), Compound 3.S.

Example 7

Preparation of-5-(4,6-dimethyl-1H-benzimidazol-2-yl)-4-methyl-N-[3-(1-methyl-4-piperidinyl)-propyl]-2-pyrimidinamine 2,3-dihydroxybutanedioate hydrate (1:0.5:4), Compound 3, from the anhydrous hemitartrate, Compound 2.1

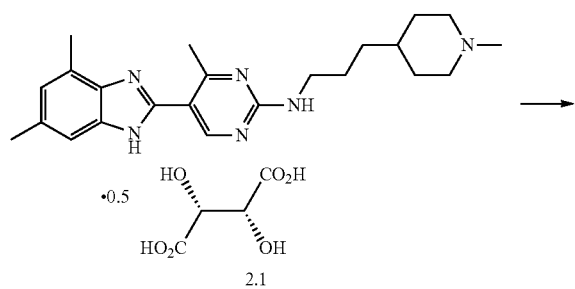

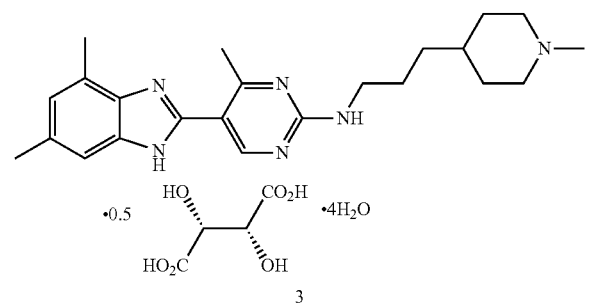

Figure 3:
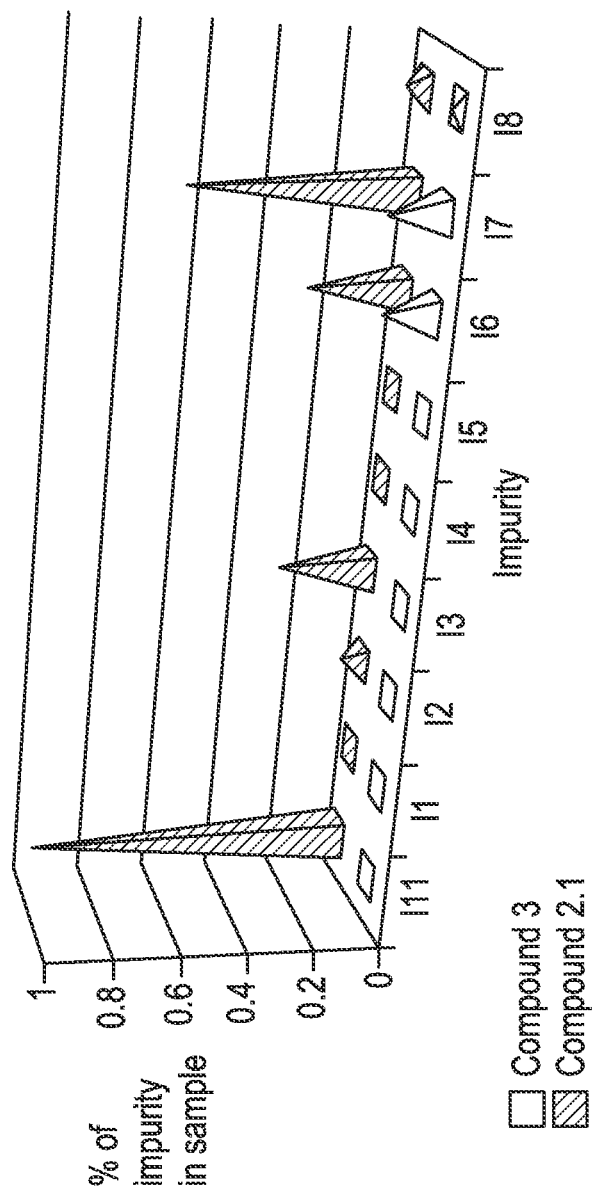
FIG. 3. Comparison of impurity segregation profiles for Compounds 2.1 and 3 (See also Example 7)

A jacketed glass reactor was charged with 5-(4,6-dimethyl-1H-benzimidazol-2-yl)-4-methyl-N-[3-(1-methyl-4-piperidinyl)propyl]-2-pyrimidinamine 2,3-dihydroxybutanedioate (1:0.5), compound 2.1 (60.0 g, 121.9 mmol) and water (280.0 g) at 20° C. The solid was dissolved by heating the reaction mixture to T≥58° C. The resultant clear, yellow solution was filtered (polish filtration) and the filter washed with water (20.0 g). The filtrate was cooled to T≤40° C. and seeded with 5-(4,6-dimethyl-1H-benzimidazol-2-yl)-4-methyl-N-[3-(1-methyl-4-piperidinyl)propyl]-2-pyrimidinamine 2,3-dihydroxybutanedioate hydrate (1:0.5:4), Compound 3.S (0.01 g). The thin suspension was stirred at T=35-40° C. for 1 h, then cooled stepwise to 5° C., resulting in the crystallization of the product. Because more than one crystallization is performed according to this invention, the crystallization referred to above for Compound 3 is sometimes refered to as a third crystallization. It is sometimes referred to as a second crystallization if Compound 2.1 has only been crystallized once. The white suspension was kept at T=5° C. for 4 h, before the product was isolated by centrifugation. The product cake was washed with water (104.0 g). The solid was dried in vacuo (200-300 mbar) at 20-30° C. for 28 h with a gas bleed to yield the title Compound 3 (95% of th. yield). This compound has an aqueous solubility of about 4.1 mg/ml at room temperature. It is stable under ambient conditions, but converts to Compound 2.2 upon dehydration by heating or in low relative humidity. The powder X-ray diffraction (XRD) profile of an embodiment of Compound 3 is shown in FIG. 4, and the XRD peak lists are shown in Tables 5, 6 and 6.1-6.3. FIG. 9 displays the XRD profiles for Compounds 2.1, 2.2 and 3. Table 4 and FIG. 3 display the impurity profiles for compounds 2.1 and 3, according to this example, which that, as noted with respect to Compound 2, that the impurity profile of Compound 3 is significantly reduced with respect to that of Compound 2.1. Embodiments of Compound 3 obtained as described in this Example 7 had purity equal to or about 99.86%. Compound 3 presents advantageous development chemistry features: The synthesis of Compound 3 provides high, reproducible yield (about 95%, compared to about 85% for Compound 2.1); it is synthesized by a simple methodology that does not require azeotropic distillation or exposure to long stirring times and heating in the presence of MeOH/EtOH, which could lead to the formation of side products; it presents high and reproducible purity, including the removal of certain amino impurities; and crystallization can be done in water as solvent, with no need for mother liquor incineration, which leads to cost saving green chemistry.

TABLE 4

Impurity Profiles of Compounds 2.1 and 3 (Example 7)

| | Compound 2.1 | Compound 3 |
|---|---|---|
| Impurity 11 (I11) | 0.98 | 0 |
| Impurity 1 (I1) | 0 | 0 |
| Impurity 2 (I2) | 0.07 | 0 |
| Impurity 3 (I3) | 0.29 | 0 |
| Impurity 4 (I4) | 0 | 0 |
| Impurity 5 (I5) | 0.03 | 0 |
| Impurity 6 (I6) | 0.29 | 0 |
| Impurity 7 (I7) | 0.67 | 0.18 |
| Impurity 8 (I8) | 0.06 | 0.02 |

TABLE 5

XRD Peak list for an embodiment of Compound 3 (Example 7) for peaks with relative intensities >5%

| Position [°2θ] | d-spacing [Å] | Intensity (counts) | Relative Intensity (%) |
|---|---|---|---|
| 6.909 | 12.79 | 19018 | 20.7 |
| 6.963 | 12.70 | 13509 | 14.7 |
| 8.692 | 10.17 | 92032 | 100.0 |
| 11.957 | 7.40 | 5763 | 6.3 |
| 12.107 | 7.31 | 51083 | 55.5 |
| 12.419 | 7.13 | 6894 | 7.5 |
| 13.956 | 6.35 | 5038 | 5.5 |
| 14.463 | 6.12 | 6922 | 7.5 |
| 15.355 | 5.77 | 6205 | 6.7 |
| 15.393 | 5.76 | 5573 | 6.1 |
| 15.755 | 5.62 | 4416 | 4.8 |
| 16.304 | 5.44 | 15526 | 16.9 |
| 16.350 | 5.42 | 14203 | 15.4 |
| 17.051 | 5.20 | 6303 | 6.8 |
| 17.442 | 5.08 | 5085 | 5.5 |
| 18.445 | 4.81 | 7903 | 8.6 |
| 18.540 | 4.79 | 5021 | 5.5 |
| 19.265 | 4.61 | 23648 | 25.7 |
| 19.861 | 4.47 | 10731 | 11.7 |
| 19.906 | 4.46 | 10331 | 11.2 |
| 21.628 | 4.11 | 10197 | 11.1 |
| 21.734 | 4.09 | 79383 | 86.3 |
| 22.514 | 3.95 | 8529 | 9.3 |
| 23.115 | 3.85 | 4787 | 5.2 |
| 23.963 | 3.71 | 11967 | 13.0 |
| 24.052 | 3.70 | 28743 | 31.2 |
| 24.352 | 3.66 | 48026 | 52.2 |
| 25.124 | 3.54 | 12475 | 13.6 |

TABLE 5-continued

XRD Peak list for an embodiment of Compound 3 (Example 7) for peaks with relative intensities >5%

| Position [°2θ] | d-spacing [Å] | Intensity (counts) | Relative Intensity (%) |
|---|---|---|---|
| 26.434 | 3.37 | 8095 | 8.8 |
| 27.012 | 3.30 | 13716 | 14.9 |
| 30.257 | 2.95 | 5159 | 5.6 |
| 30.297 | 2.95 | 6434 | 7.0 |
| 30.449 | 2.94 | 7306 | 7.9 |

TABLE 6

XRD Peak list for an embodiment of Compound 3 (Example 7) for peaks with relative intensities >10%

| Position [°2θ] | d-spacing [Å] | Intensity (counts) | Relative Intensity (%) |
|---|---|---|---|
| 6.909 | 12.79 | 19018 | 20.7 |
| 6.963 | 12.70 | 13509 | 14.7 |
| 8.692 | 10.17 | 92032 | 100.0 |
| 12.107 | 7.31 | 51083 | 55.5 |
| 16.304 | 5.44 | 15526 | 16.9 |
| 16.350 | 5.42 | 14203 | 15.4 |
| 19.265 | 4.61 | 23648 | 25.7 |
| 19.861 | 4.47 | 10731 | 11.7 |
| 19.906 | 4.46 | 10331 | 11.2 |
| 21.628 | 4.11 | 10197 | 11.1 |
| 21.734 | 4.09 | 79383 | 86.3 |
| 23.963 | 3.71 | 11967 | 13.0 |
| 24.052 | 3.70 | 28743 | 31.2 |
| 24.352 | 3.66 | 48026 | 52.2 |
| 25.124 | 3.54 | 12475 | 13.6 |
| 27.012 | 3.30 | 13716 | 14.9 |

TABLE 6.1

XRD Peak list for an embodiment of Compound 3 (Example 7) for peaks with relative intensities >50%

| Position [°2θ] | d-spacing [Å] | Intensity (counts) | Relative Intensity (%) |
|---|---|---|---|
| 8.692 | 10.17 | 92032 | 100.0 |
| 12.107 | 7.31 | 51083 | 55.5 |
| 21.734 | 4.09 | 79383 | 86.3 |
| 24.352 | 3.66 | 48026 | 52.2 |

TABLE 6.2

XRD Peak list for an embodiment of Compound 3 (Example 7) for peaks with relative intensities >20%

| Position [°2θ] | d-spacing [Å] | Intensity (counts) | Relative Intensity (%) |
|---|---|---|---|
| 6.909 | 12.79 | 19018 | 20.7 |
| 8.692 | 10.17 | 92032 | 100.0 |
| 12.107 | 7.31 | 51083 | 55.5 |
| 19.265 | 4.61 | 23648 | 25.7 |
| 21.734 | 4.09 | 79383 | 86.3 |
| 24.052 | 3.70 | 28743 | 31.2 |
| 24.352 | 3.66 | 48026 | 52.2 |

TABLE 6.3

XRD Peak list for an embodiment of Compound 3 (Example 7) for peaks with relative intensities of at least 13%

| Position [°2θ] | d-spacing [Å] | Intensity (counts) | Relative Intensity (%) |
|---|---|---|---|
| 6.909 | 12.79 | 19018 | 20.7 |
| 6.963 | 12.70 | 13509 | 14.7 |
| 8.692 | 10.17 | 92032 | 100.0 |
| 12.107 | 7.31 | 51083 | 55.5 |
| 16.304 | 5.44 | 15526 | 16.9 |
| 16.350 | 5.42 | 14203 | 15.4 |
| 19.265 | 4.61 | 23648 | 25.7 |
| 21.734 | 4.09 | 79383 | 86.3 |
| 23.963 | 3.71 | 11967 | 13.0 |
| 24.052 | 3.70 | 28743 | 31.2 |
| 24.352 | 3.66 | 48026 | 52.2 |
| 25.124 | 3.54 | 12475 | 13.6 |
| 27.012 | 3.30 | 13716 | 14.9 |

Example 8

Recrystallization of-5-(4,6-dimethyl-1H-benzimidazol-2-yl)-4-methyl-N-[3-(1-methyl-4-piperidinyl)-propyl]-2-pyrimidinamine 2,3-dihydroxybutanedioate hydrate (1:0.5:4), Compound 3

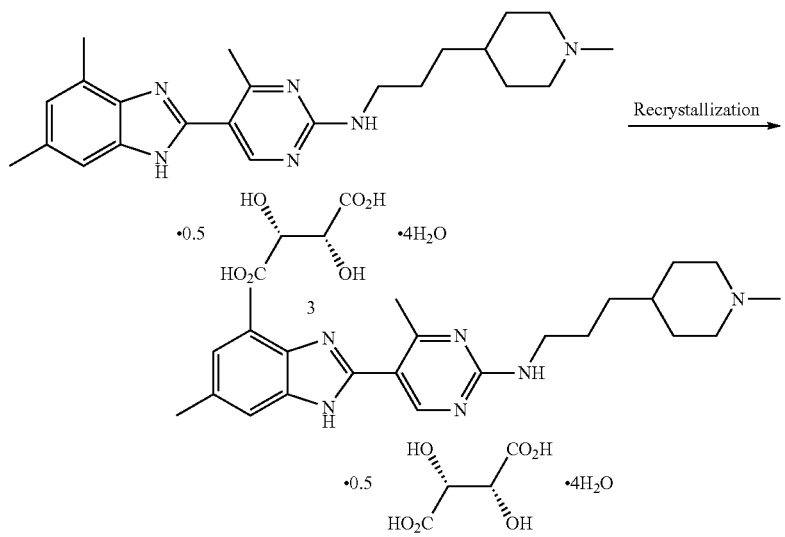

In a 500 mL glass reactor equipped with a temperature probe and mechanical stirrer, 5-(4,6-dimethyl-1H-benzimidazol-2-yl)-4-methyl-N-[3-(1-methyl-4-piperidinyl)propyl]-2-pyrimidinamine 2,3-dihydroxy-butanedioate hydrate (1:0.5:4), compound 3 (Example 5) (72.0 g, 133.4 mmol) was slurried in water (400.0 g) at 15-25° C. The white suspension was then heated to 60° C. within ca. 30 min to dissolve the solid completely. To the resultant yellowish solution was then added a suspension of seeding crystals (0.36 g, 5-(4,6-dimethyl-1H-benzimidazol-2-yl)-4-methyl-N-[3-(1-methyl-4-piperidinyl)propyl]-2-pyrimidinamine 2,3-dihydroxybutanedioate hydrate (1:0.5:4), compound 3.S, in 2 mL water, stirred at 20-25° C. for 1 h). The thin suspension was kept at 40° C. for approximately 1 h, then cooled stepwise to 5° C. within a minimum of 9 h. It was kept at 5° C. overnight, before the product was isolated by centrifugation. Because more than one crystallization is performed according to this invention, the recrystallization referred to above for Compound 3 is sometimes refered to as a fourth crystallization. It is sometimes referred to as a third crystallization when Compound 2.1 has only been crystallized once. The product cake was washed with water (99.0 g). The wet product was dried at room temperature/ambient pressure for 5 days to yield the title Compound 3 (97% yield), recrystallized. After recrystallization according to this Example 8, Compound 3, that in the pre-crystallization stage had a purity of 99.86%, had purity equal to or about 99.90%. Purity changes upon recrystallization of Compound 3 are shown in Table 7.

TABLE 7

| Impurity | m/z [M + H]+ | Relative retention time (RRT) | Average impurities (%) in Compound 3 before recrystallization | Average impurities (%) in Compound 3 before recrystallization |
|---|---|---|---|---|
| I1 | 278 | 0.32 | n. d. | n. d. |
| A2 | 276 | 0.48 | n. d. | n. d. |
| I3 | 277 | 0.73 | n. d. | n. d. |
| A4 | 395 | 0.81 | n. d. | n. d. |
| I5 | 653 | 0.86 | 0.02 | n. d. |
| A6 | unk | 0.87 | n. d. | n. d. |
| A7 | 274/733 | 0.89 | n. d. | n. d. |
| A8a & A8b | 653/unk | 0.91 | n. d. | n. d. |
| I8 | 505 | 0.93 | n. d. | n. d. |
| A10 | unk | 0.95 | n. d. | n. d. |
| A11 | unk | 0.97 | n. d. | n. d. |
| A12 | unk | 0.98 | n. d. | n. d. |
| Compound 3 | 393 | 1.00 | 99.86 | 99.90 |
| A13 | unk | 1.03 | n. d. | n. d. |
| I7 | 407 | 1.04 | 0.06 | 0.05 |
| A15 | unk | 1.048 | n. d. | n. d. |
| A16 | unk | 1.057 | n. d. | n. d. |
| A17 | unk | 1.064 | n. d. | n. d. |
| A18a & A18b | 512/409 | 1.07 | n. d. | 0.02 |
| A19 | unk | 1.08 | n. d. | n. d. |
| A20 | unk | 1.10 | n. d. | n. d. |
| A21 | unk | 1.14 | 0.04 | 0.04 |
| A22 | 847 | 1.17 | n. d. | n. d. |

Abbreviations used in the immediately preceding Table: nd = not detected, unk = unknown, na = not analyzed Example 9

Preparation of 5-(4,6-dimethyl-1H-benzimidazol-2-yl)-4-methyl-N-[3-(1-methyl-4-piperidinyl)-propyl]-2-pyrimidinamine fumarate methanolate (1:2:1), Compound 4

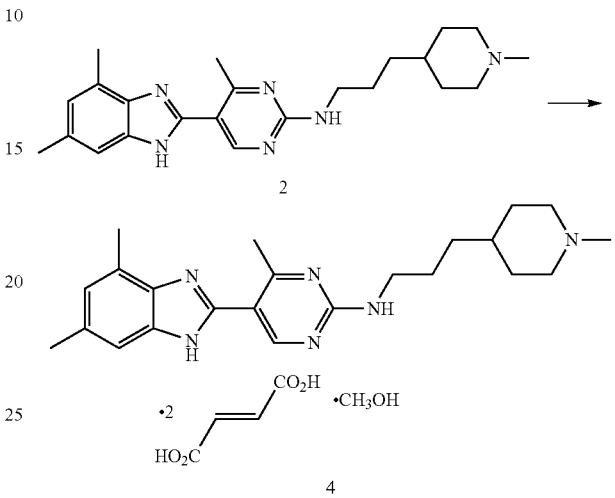

Figure 5:
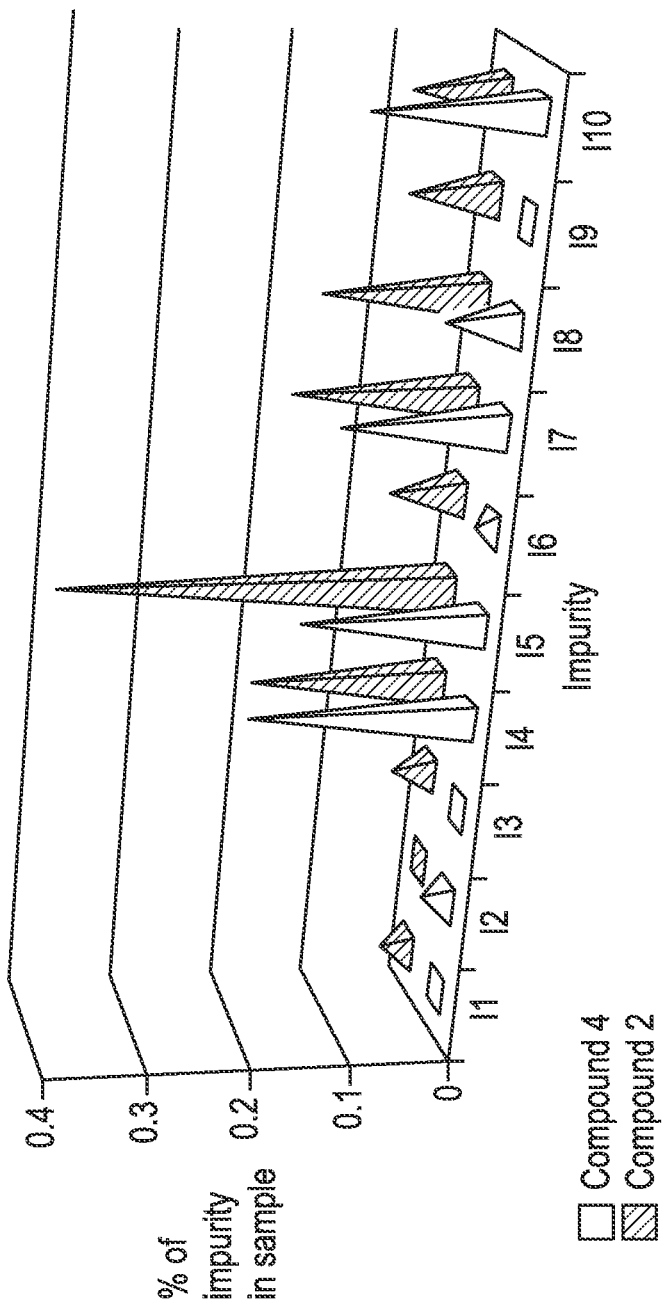
FIG. 5. Comparison of impurity segregation profiles for Compounds 2 and 4 (See also Example 9)

To a 500 mL Erlenmeyer flask which contained 10.012 g (0.0255 mol) of 5-(4,6-dimethyl-1H-benzimidazol-2-yl)-4-methyl-N-[3-(1-methyl-4-piperidinyl)propyl]-2-pyrimidinamine), compound 2, was added 6.2155 g of fumaric acid (2.1 equivalents) and a stir bar. To that solid mixture, about 300 mL of 1:1 (weight ratio) hot MeOH:EtOAc were added while heating and stirring. The term "hot solvent" is used here so that such solvent is warm based on such solvent boiling point. In some embodiments, hot MeOH:EtOAc was used at a temperature of about 50° C. to 60° C. Additional solvent can be added until all the solids are completely dissolved. The solution mixture was allowed to heat at boiling temperature for another 10 min to give a yellow homogenous solution. The reaction mixture was removed from the heating plate and allowed to cool down to room temperature (rt) on the bench top. Precipitate formed as clusters in the bottom of the flask after 2 days. 13.0702 g of 5-(4,6-dimethyl-1H-benzimidazol-2-yl)-4-methyl-N-[3-(1-methyl-4-piperidinyl)-propyl]-2-pyrimidinamine fumarate methanolate (1:2:1), compound 4, as a light yellow solid crystalline were collected by vacuum filter. XRD profiles confirmed the unique pattern of the desired fumarate salt and according to IR-off gas analysis, this material is a methanol solvate of the fumarate salt (4.1% weight loss). Table 8 and FIG. 5 display the impurity profiles for compounds 2 and 4.

In contrast with the observations made in Examples 5 and 7, embodiments of Compound 4 obtained as described in this Example 9 had impurity profiles that do not present an overall improvement with respect to that of Compound 2. In addition, assays of embodiments of this fumarate salt indicated varying compositions including mixtures of mono- and di-fumarate. Furthermore, fumaric acid presents comparatibly lower solubility in solvents that are typically preferable for salt formation.

TABLE 8

Impurity Profile of Compounds 2 and 4 (Example 9)

| | Compound 2 | Compound 4 |
|---|---|---|
| Impurity 1 (I1) | 0.03 | 0 |
| Impurity 2 (I2) | 0 | 0.03 |
| Impurity 3 (I3) | 0.04 | 0 |
| Impurity 4 (I4) | 0.18 | 0.22 |
| Impurity 5 (I5) | 0.37 | 0.18 |
| Impurity 6 (I6) | 0.07 | 0.02 |
| Impurity 7 (I7) | 0.17 | 0.16 |
| Impurity 8 (I8) | 0.15 | 0.07 |
| Impurity 9 (I9) | 0.08 | 0 |
| Impurity 10 (I10) | 0.09 | 0.16 |

Example 10

Preparation of 5-(4,6-dimethyl-1H-benzimidazol-2-yl)-4-methyl-N-[3-(1-methyl-4-piperidinyl)-propyl]-2-pyrimidinamine phosphate (1:1), Compound 5

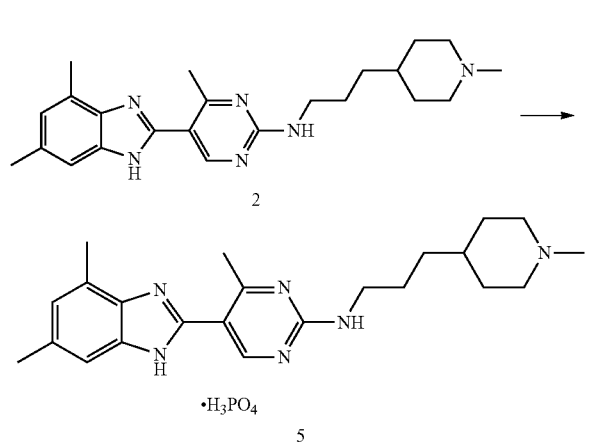

To a 50 mL Erlenmeyer flask which contained 500.32 mg (1.275 mmol) of 5-(4,6-dimethyl-1H-benzimidazol-2-yl)-4-methyl-N-[3-(1-methyl-4-piperidinyl)propyl]-2-pyrimidinamine), Compound 2 and a stir bar, was added about 20 mL of hot 50:50 MeOH:EtOH solvent. In some embodiments, hot MeOH:EtOH was used at a temperature of about 50° C. to 60° C. A clear yellow solution was obtained. The solution was brought to boiling temperature on a hot plate with stirring, and 96 μL of phosphoric acid (85% in water, 1.1 equivalent) was added dropwise. The reaction mixture became cloudy as the acid was added but quickly changed to a clear yellow solution as it was stirred. The reaction mixture was left to heat on the hot plate at low temperature for another 10 min before being removed and allowed to cool down to rt on the bench top. The flask was left at room temperature overnight to allow crystals to precipitate. For this experiment, small spatula of the phosphate salt was added to the reaction mixture as seeded and left open at rt overnight to form crystals. Very fine crystalline needles are formed in the bottom of the flask after 2 days. 531.3 mg (85% yield) of the off white, light yellow solid crystalline 5-(4,6-dimethyl-1H-benzimidazol-2-yl)-4-methyl-N-[3-(1-methyl-4-piperidinyl)-propyl]-2-pyrimidinamine phosphate (1:1), compound 5 were collected by vacuum filter. Precipitation will occur at rt after 2 days or more without seeding, but it forms an oil layer in the bottom of the flask if left at cold temperature (5° C.). Significant losses in the mother liquor were observed in some embodiments. Furthermore, this phosphate salt tended to form a sticky oil on the reactor walls, which makes it more difficult to handle than any of Compounds 2.1 and 3. XRD profiles confirmed the pattern of the desired phosphate salt. As to purity, this phosphate salt did not show improved impurity segregaton ability with respect to that of Compound 2.1.

Examples 2-5 and 7 describe synthetic methodologies according to this invention for compounds such as the following compounds:

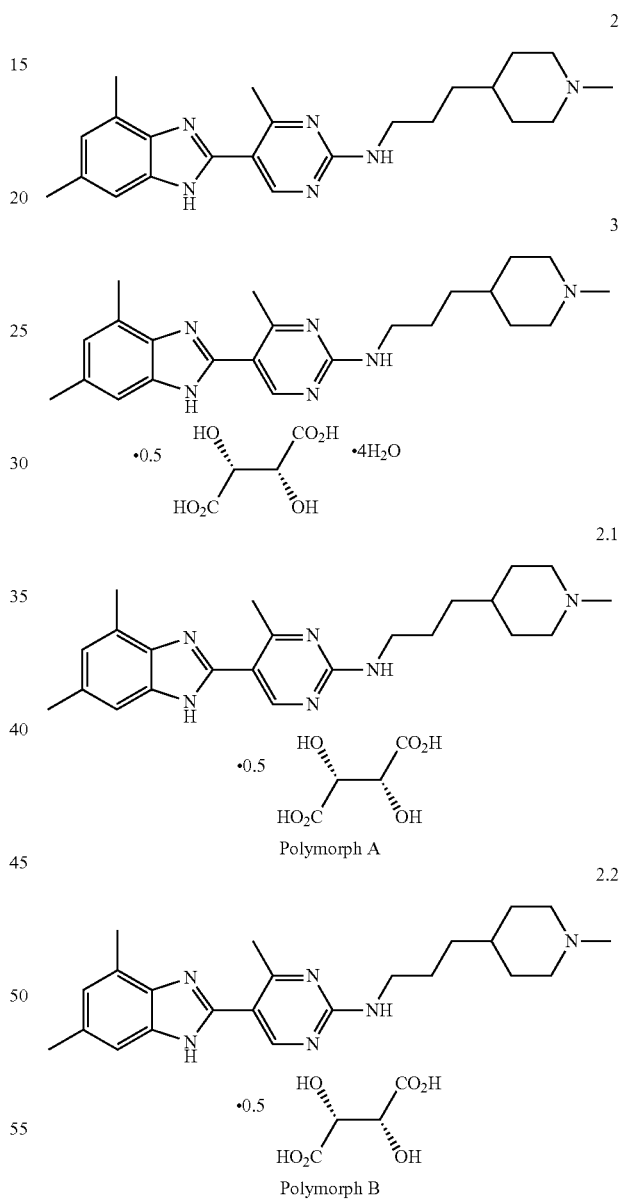

In addition to the impurity segregation features of various of such compounds as noted in preceding Examples, it is also noted that pharmaceutically acceptable salts of Compound 2 are generally preferable for pharmaceutical use to formulations of the free base Compound 2 itself. Furthermore, Compound 3 presents itself as a well characterized form which is generally preferable to anhydrous salts, such as Compounds 2.1 and 2.2, that present themselves in more than one form (such as polymorphs A and B, respectively). When Compound 3 was made either from the free base Compound 2 (Example 5) or from the anhydrous hemi-tartrate Compound 2.1 (Example 7), Compound 3 was found to be highly pure at about 99.86% purity. An additional recrystallization improved its purity to about 99.90%, and no other salt forms where found upon such recrystallization. Because no conversion of Compound 3 to other forms was detected, this compound provides the advantageous possibility of performing with it aqueous-based formulation development, such as wet granulation work. Whereas a re-crystallization of Compound 2.1 is described herein, see Example 3, step E, the impurity segregation properties of Compound 3 are such that its synthesis in the high degrees of purity exemplified herein does not have to rely on a re-crystallization of such Compound 2.1, which is presented in the foregoing examples for illustrative purposes.

Example 11

Some Impurity Structural Formulae and Characterizations

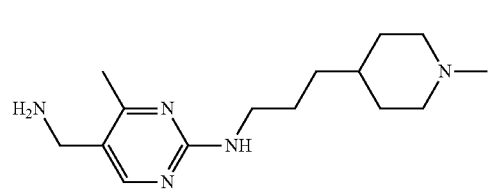
(I1)

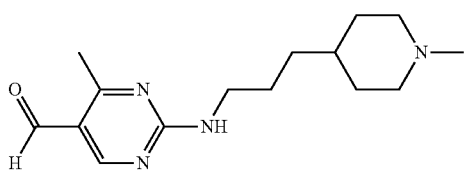
(I3)

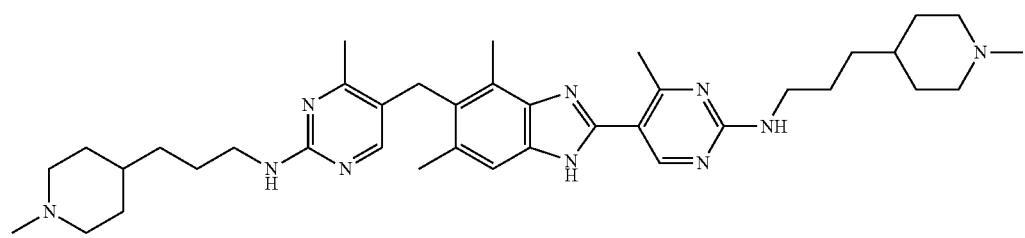
(I5)

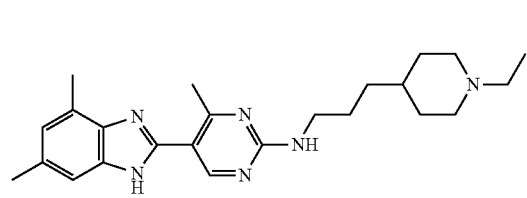
(I7)

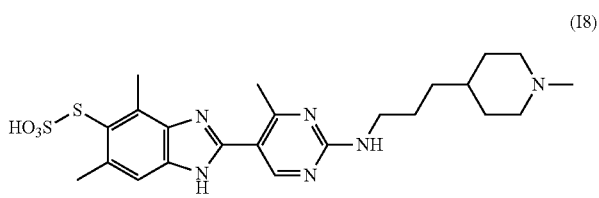
(I8)

TABLE 9

| Impurity Designation | Characterization |
|---|---|
| I1 | Molecular weight 277, Compound of structure I1 |
| I2 | Molecular weight 394. |
| I3 | Molecular weight 276, Compound of structure I3 |
| I4 | Molecular weight 652. |
| I5 | Molecular weight 652, Compound of structure I5 |
| I6 | Molecular weight 732. |
| I7 | Molecular weight 406, Compound of structure I7 |
| I8 | Molecular weight 504, Compound of structure I8 |
| I9 | Relative retention time is 1.07. |
| I10 | Relative retention time is 1.37. |
| I11 | Molecular weight estimate is 277 |

When the material being referred to herein is characterized by saying that any given impurity content is "0", or that such given impurity is not detected, typically abbreviated as "n.d." or "nd", then such material is also referred to as being "substantially free from" any such given impurity.

Impurities were analyzed according to standard high performance liquid chromatography (HPLC) with detection by mass spectrometry (MS) or ultra-violet spectroscopy (UV), finding one or more of the impurity's mass, relative retention time, and amount (as relative area percentage), and they are provided herein by using notation that is typical in such standard methodologies. For an illustrative review of the same, see for example, S. Levin, "High Performance Liquid Chromatography (HPLC) in the pharmaceutical analysis", Medtechnia (February 2010), which is incorporated herein by reference (describing HPLC modes, HPLC theory, the role of HPLC in drug analysis, and specialized HPLC separations; available at, for example, http://www.forumsci.co.il/HPLC/WEBPharm_Review/HPLC_pharma_Modes-RP.html).

Impurity amounts as reported herein were determined at a level below the level allowed in this industry standards. For example, in a validation of the impurity analysis method of Compound 2, a relative standard deviation of not more than 4% was found (i.e., if the impurity amount y in this case were 0.05%, a relative standard deviation of not more than 4% would mean y to be 0.05±0.002%).

While the invention has been illustrated by reference to examples, it is understood that the invention is intended not to be limited to the foregoing detailed description.

What is claimed is:

1. A method of obtaining a purified pharmaceutically acceptable salt of a [5-(4,6-dimethyl-1H-benzoimidazol-2-yl)-4-methyl-pyrimidin-2-yl]-[3-(1-methyl-piperidin-4-yl)-propyl]-amine, comprising:

forming a hemitartrate salt of the compound of formula (2):

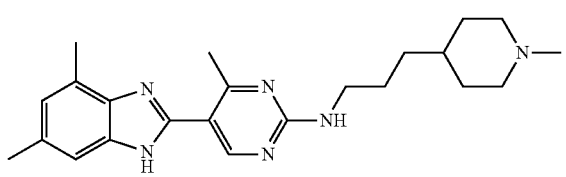

(2)

in a low-alkyl alcohol solvent to yield a hemitartrate salt alcohol mixture;

a first crystallizing out of said mixture the solid hemitartrate of formula 2.1:

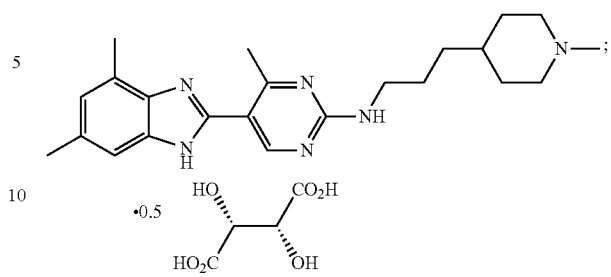

(2.1)

dissolving said solid hemitartrate in a low-alkyl alcohol-containing medium to yield a low-alkyl alcohol-containing hemitartrate solution;

a second crystallizing out of said hemitartrate solution a re-crystallized hemitartrate of formula 2.1;

dissolving said hemitartrate in water to yield an aqueous hemitartrate solution;

seeding said aqueous solution with crystal seeds of the tetrahydrate of said hemitartrate; and a third crystallizing said aqueous hemitartrate solution to form the solid tetrahydrate hemitartrate of formula (3):

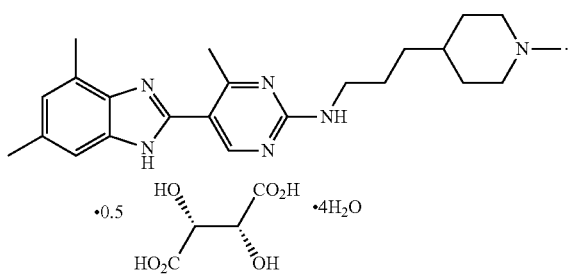

(3)

2. A method as in claim 1, wherein said third crystallizing is performed once, and said tetrahydrate hemitartrate of formula (3) has a puritiy of at least about 99%.

3. A method as in claim 1, wherein said third crystallizing is performed once, and said tetrahydrate hemitartrate of formula (3) has a puritiy of at least about 99.5%.

4. A method as in claim 1, wherein third crystallizing is performed once, and said tetrahydrate hemitartrate of formula (3) has a puritiy of at least about 99.8%.

5. A method as in claim 1, further comprising:
dissolving said tetrahydrate hemitartrate of formula (3) in water to form an aqueous tetrahydrate hemitartrate product solution;
seeding said aqueous tetrahydrate hemitartrate product solution with crystal seeds of the tetrahydrate of said hemitartrate; and
a fourth crystallazing said aqueous tetrahydrate hemitartrate product solution to yield a re-crystallized tetrahydrate hemitartrate of formula (3).

6. A method as in claim 5, wherein said fourth crystallizing is performed once, and said re-crystallized tetrahydrate hemitartrate of formula (3) has a purity of at least about 99.9%.

7. A method as in claim 2, further comprising:
dissolving said hemitartrate in water to yield an aqueous hemitartrate solution;
seeding said aqueous solution with crystal seeds of the tetrahydrate of said hemitartrate; and a second crystallizing said aqueous hemitartrate solution to form the solid tetrahydrate hemitartrate of formula (3):

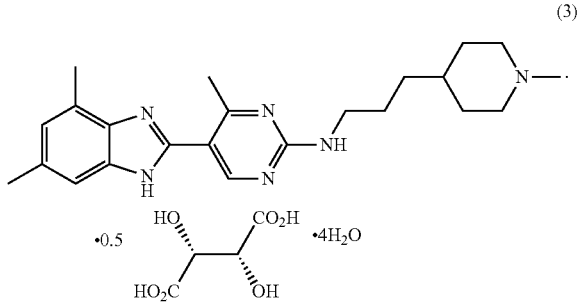

(3)

8. A method as in claim 7, wherein said third crystallizing is performed once, and said tetrahydrate hemitartrate of formula (3) has a puritiy of at least about 99%.

9. A method as in claim 7, further comprising:

dissolving said tetrahydrate hemitartrate of formula (3) in water to form an aqueous tetrahydrate hemitartrate product solution;

seeding said aqueous tetrahydrate hemitartrate product solution with crystal seeds of the tetrahydrate of said hemitartrate; and a third crystallazing said aqueous tetrahydrate hemitartrate product solution to yield a re-crystallized tetrahydrate hemitartrate of formula (3).

10. A method as in claim 7, wherein said third crystallizing is performed once, and said re-crystallized tetrahydrate hemitartrate of formula (3) has a purity of at least about 99.5%.

11. A method as in claim 1, wherein said third crystallizing comprises performing the following operations with said aqueous hemitartrate solution: Stirring at about 35-40° C. for about four hours, and cooling to about 5° C.

12. A method as in claim 5, wherein said fourth crystallizing comprises performing the following operations with said product solution: Keeping it at about 40° C. for about one hour, and subsequently cooling to about 5° C.

13. A method as in claim 7, wherein said second crystallizing comprises performing the following operations with said aqueous hemitartrate solution: Stirring at about 35-40° C. for about one hour, and subsequently cooling to about 5° C.

14. A method as in claim 9, wherein said third crystallizing comprises performing the following operations with said aqueous hemitartrate solution: Keeping it at about 40° C. for about one hour, and subsequently cooling to about 5° C.

* * * * *